(12) United States Patent  (10) Patent No.: US 8,001,373 B2
Honda  (45) Date of Patent: Aug. 16, 2011

(54) RECEIVING APPARATUS AND IN-VIVO INFORMATION ACQUIRING SYSTEM EMPLOYING THE SAME

(75) Inventor: Takemitsu Honda, Tokyo (JP)

(73) Assignee: Olympus Medical Systems Corp. (JP)

( * ) Notice: Subject to any disclaimer, the term of this patent is extended or adjusted under 35 U.S.C. 154(b) by 923 days.

(21) Appl. No.: 11/617,488

(22) Filed: Dec. 28, 2006

(65) Prior Publication Data

US 2007/0150728 A1  Jun. 28, 2007

(30) Foreign Application Priority Data

Dec. 28, 2005 (JP) ................................ 2005-380451

(51) Int. Cl.
H04L 29/06 (2006.01)
(52) U.S. Cl. ....................................................... 713/161
(58) Field of Classification Search ................... 713/161
See application file for complete search history.

(56) References Cited

U.S. PATENT DOCUMENTS 6,346,886 B1 * 2/2002 De La Huerga ........... 340/573.1
7,319,781 B2 * 1/2008 Chen et al. .................... 382/128

FOREIGN PATENT DOCUMENTS

| JP | 2003-019111 | 1/2003 |
| JP | 2004-337596 | 12/2004 |
| JP | 2005-296186 | 10/2005 |
| JP | 2005-304512 | 11/2005 |

OTHER PUBLICATIONS

Japanese Office Action mailed Apr. 26, 2011 in connection with corresponding Japanese Patent Application No. 2005-380451.
Partial English translation of Japanese Office Action issued in connection with corresponding Japanese application provided as an explanation of prior art relevancy.

* cited by examiner

Primary Examiner — Jacob Lipman
(74) Attorney, Agent, or Firm — Ostrolenk Faber LLP

(57) ABSTRACT

A receiving apparatus includes a receiving unit which receives image data acquired through image capturing by a capsule endoscope introduced inside a subject; a reader to which a portable recording medium on which identification information identifying the subject is recorded in an erasable manner is detachably connected, the reader reading out the identification information of the subject in the recording medium; a display unit which displays the identification information of the subject read out by the reader; and a control unit which controls registration of the identification information of the subject displayed by the display unit and erasure of the registered identification information of the subject remaining in the recording medium.

31 Claims, 21 Drawing Sheets

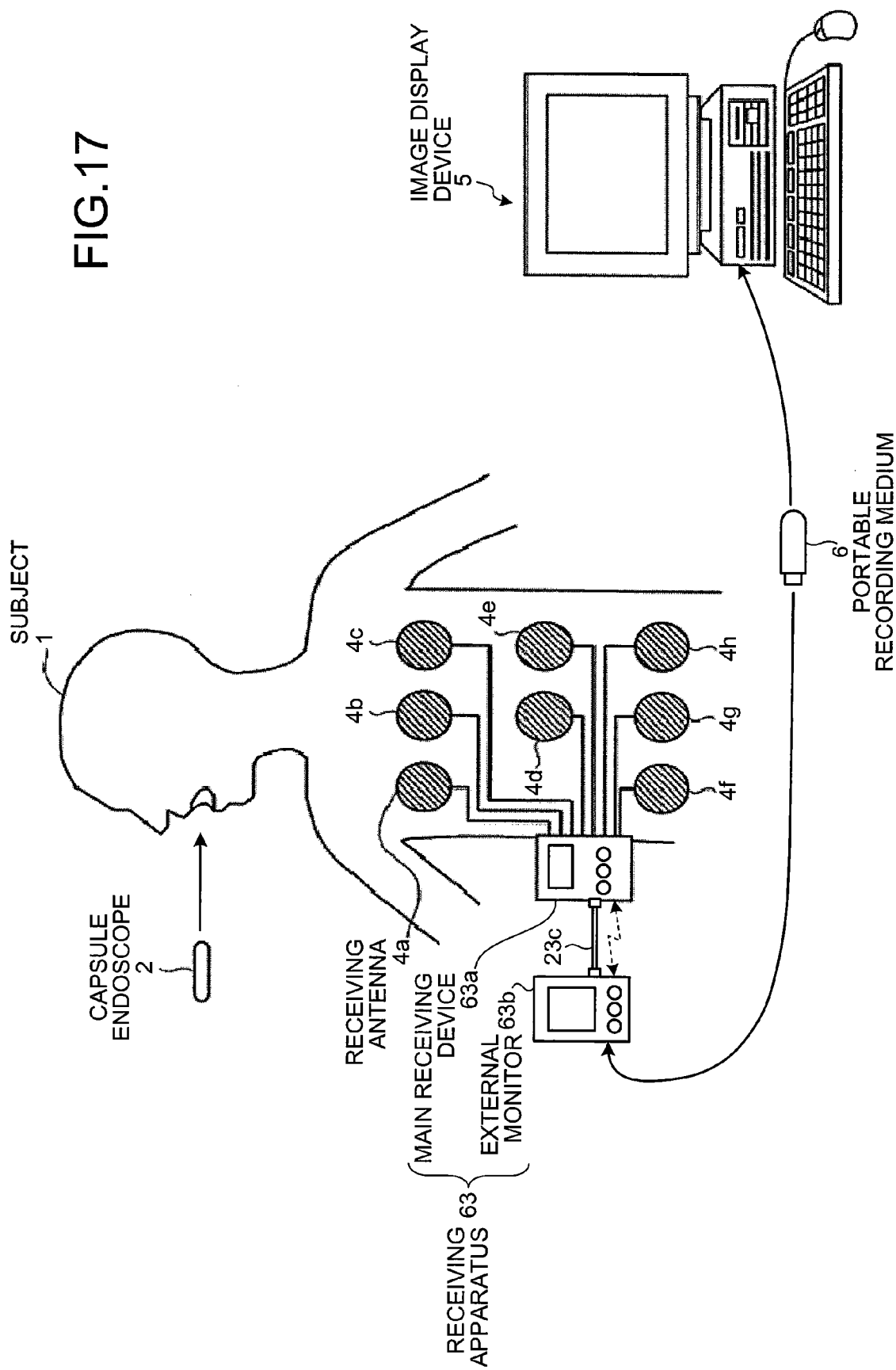

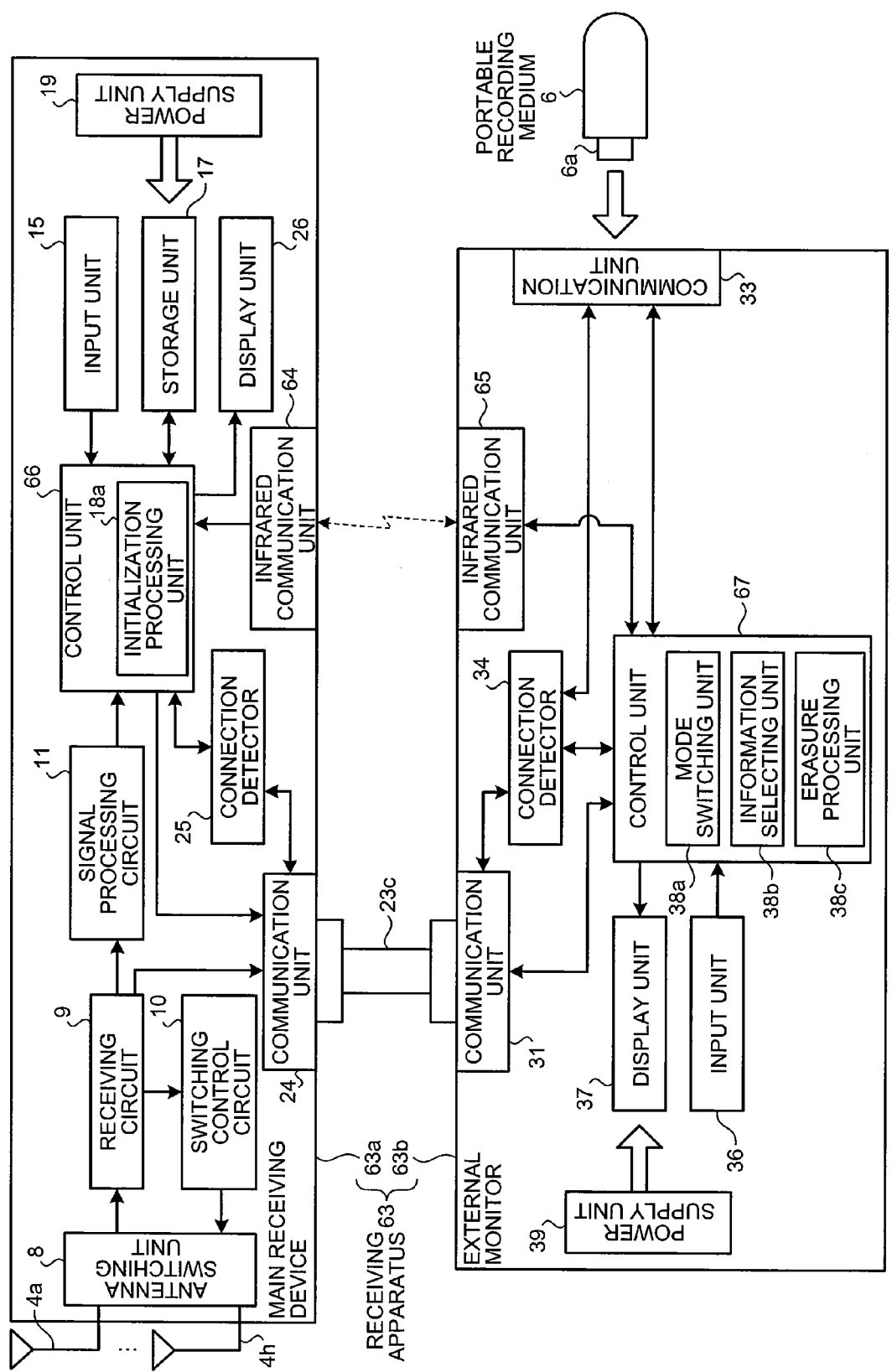

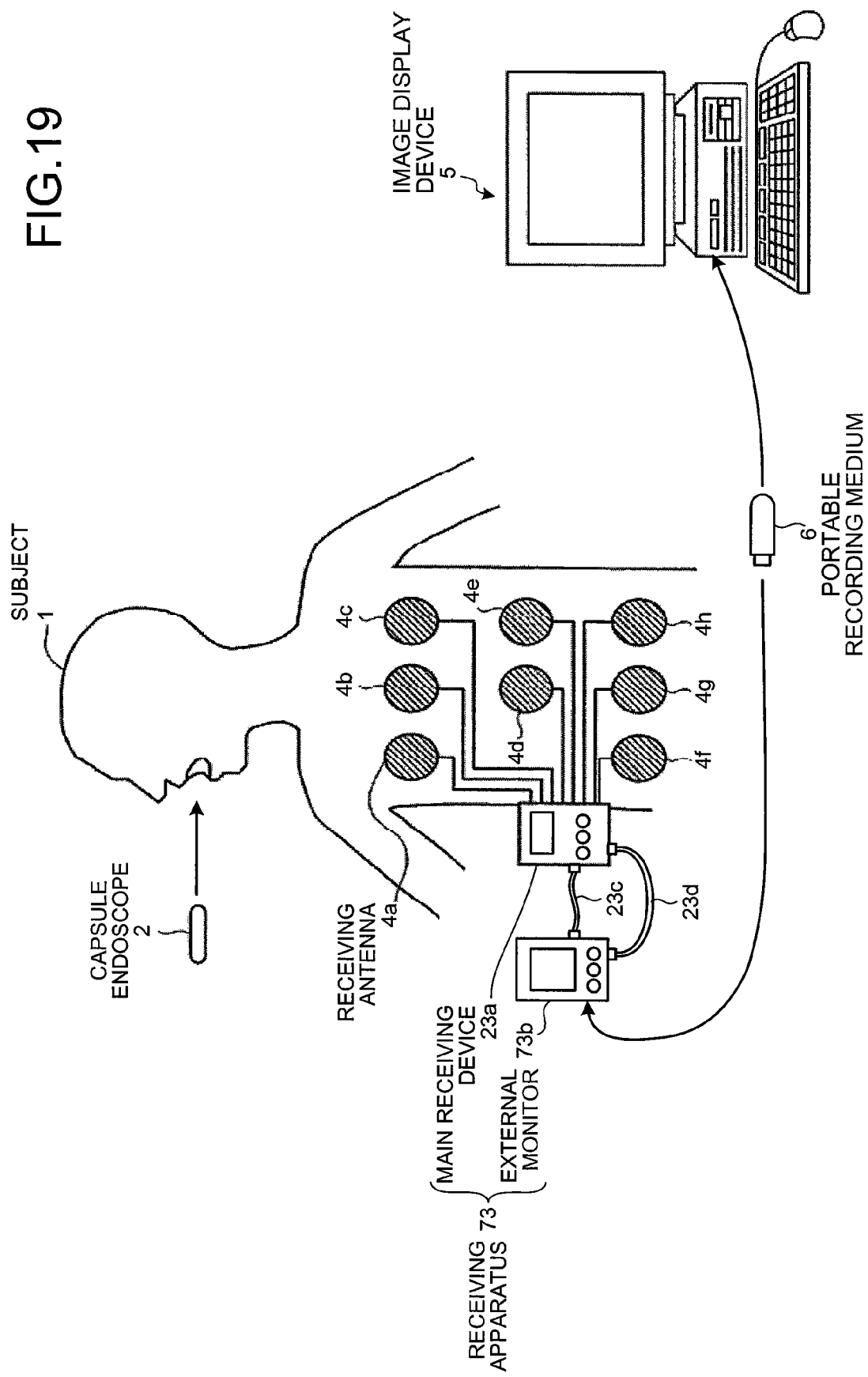

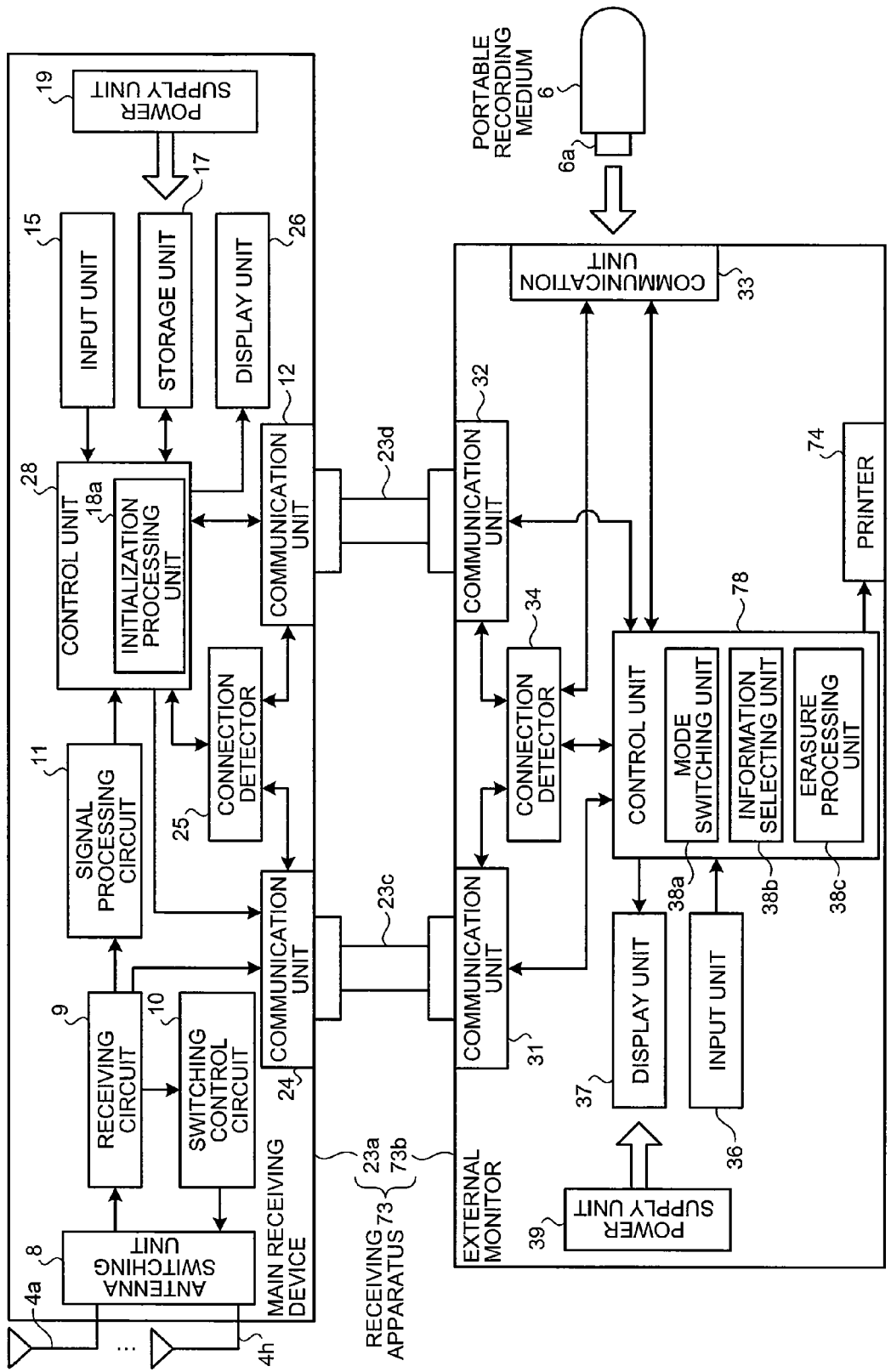

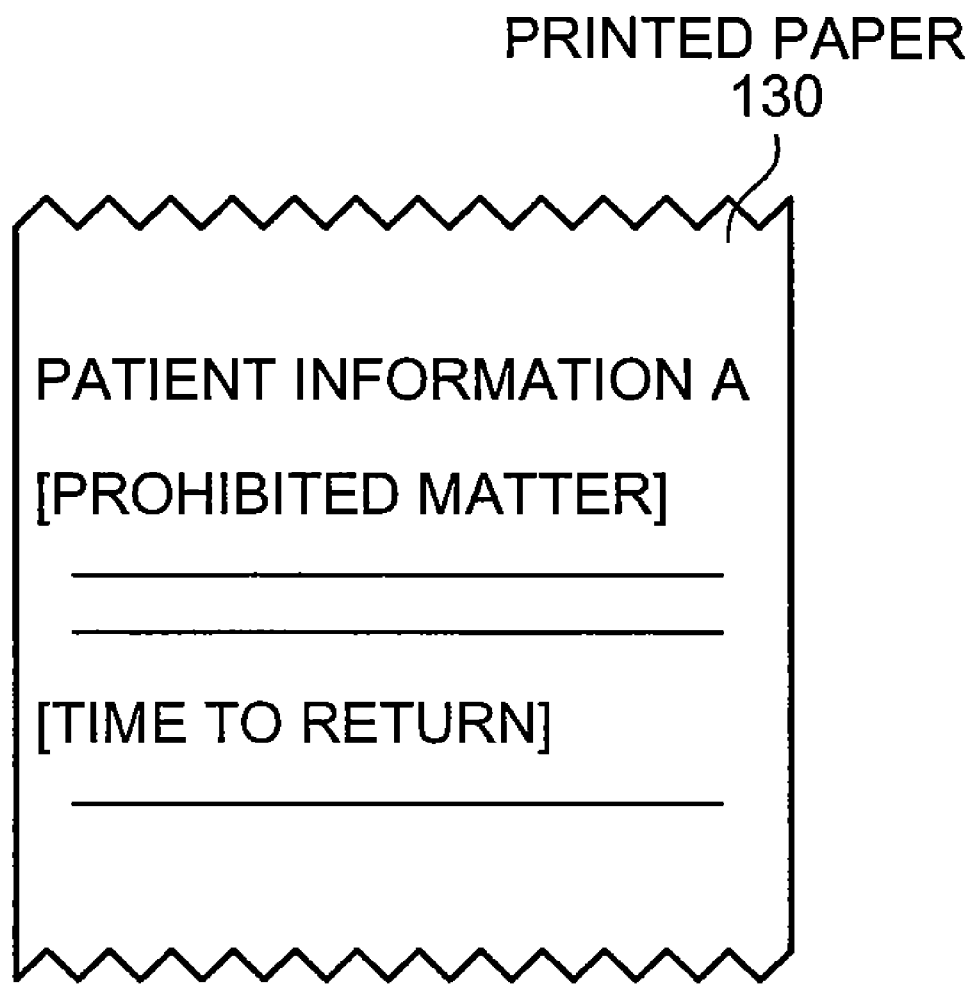

RECEIVING APPARATUS AND IN-VIVO INFORMATION ACQUIRING SYSTEM EMPLOYING THE SAME

CROSS-REFERENCE TO RELATED APPLICATIONS

This application is based upon and claims the benefit of priority from Japanese Patent Application No. 2005-380451, filed Dec. 28, 2005, the entire contents of which are incorporated herein by reference.

BACKGROUND OF THE INVENTION

1. Field of the Invention

The present invention relates to a receiving apparatus which receives image data acquired through image capturing by a capsule endoscope introduced inside a body of a subject via a predetermined electric wave, and an in-vivo information acquiring system employing the receiving apparatus.

2. Description of the Related Art

In recent years, in a field of an endoscope, a capsule endoscope, which is a swallowable endoscope provided with an imaging function and a radio communication function, appears, and an in-vivo information acquiring system which acquires image data acquired through image capturing by the capsule endoscope inside the subject is being developed. In the in-vivo information acquiring system, the capsule endoscope functions, after being swallowed from a mouth of the subject for an observation (examination) until naturally discharged from the subject, so as to travel inside digestive tracts of the subject following peristaltic movements and to capture images inside the digestive tracts at predetermined intervals, for example at 0.5-second intervals.

While the capsule endoscope travels inside the digestive tract of the subject, image data acquired through image capturing by the capsule endoscope is sequentially transmitted to an outside by radio communication, and received by a receiving apparatus via receiving antennas arranged outside the subject in a dispersed manner. The receiving apparatus generates image data based on radio signals sequentially received via the receiving antennas and sequentially accumulates the obtained image data in a memory. Thus, the receiving apparatus acquires image data of an interior of the subject from the capsule endoscope. The subject, by carrying the receiving apparatus, can move freely while having the receiving apparatus receive the image data of an interior of the digestive tract, after swallowing the capsule endoscope until naturally discharging the same. Thereafter, a doctor or a nurse transfers the image data of the interior of the subject accumulated in the receiving apparatus to an image display device and displays images of the interior of the subject on a monitor of the image display device. The doctor or the nurse can make diagnosis of the subject by observing the images of the interior of the subject as displayed on the monitor (for example, see Japanese Patent Application Laid-Open No. 2003-19111).

Before receiving the image data from the capsule endoscope introduced inside the subject, the receiving apparatus acquires patient information such as a name of a patient and a patient ID that identifies the subject, and is initialized so as to receive image data from the capsule endoscope as image data of the subject identified by the patient information. The patient information is generally managed in an integrated manner by the above mentioned image display device. The receiving apparatus is connected to the image display device installed in a medical office, for example, and acquires the patient information of the subject from the image display device for initialization. Thereafter, the initialized receiving apparatus is carried into an examination room, for example, and attached to the subject in the examination room.

SUMMARY OF THE INVENTION

A receiving apparatus according to one aspect of the present invention includes a receiving unit which receives image data acquired through image capturing by a capsule endoscope introduced inside a subject; a reader to which a portable recording medium on which identification information identifying the subject is recorded in an erasable manner is detachably connected, the reader reading out the identification information of the subject in the recording medium; a display unit which displays the identification information of the subject read out by the reader; and a control unit which controls registration of the identification information of the subject displayed by the display unit and erasure of the registered identification information of the subject remaining in the recording medium.

A receiving apparatus according to another aspect of the present invention includes an external display unit which includes a recording medium on which identification information identifying a subject is recorded in an erasable manner and a display unit which displays the identification information of the subject in the recording medium; and a main receiving device which includes a receiving unit which is detachably connected to the external display unit and receives image data acquired through image capturing by a capsule endoscope introduced inside the subject, and a control unit which controls registration of the identification information of the subject displayed by the display unit and erasure of the registered identification information of the subject remaining in the recording medium.

An in-vivo information acquiring system according to still another aspect of the present invention includes a portable recording medium on which identification information identifying a subject is recorded in an erasable manner; and a receiving apparatus which is detachably connected to the recording medium, displays the identification information of the subject read out from the recording medium, registers the identification information of the subject displayed, erases the registered identification information of the subject remaining in the recording medium, and receives image data acquired through image capturing by a capsule endoscope inside the subject.

An in-vivo information acquiring system according to still another aspect of the invention includes an external display unit which includes a recording medium on which identification information identifying a subject is recorded in an erasable manner and a display unit that displays the identification information of the subject in the recording medium, and a main receiving device which includes a receiving unit that is detachably connected to the external display unit and receives the image data acquired through image capturing by a capsule endoscope inside the subject, and a control unit which controls registration of the identification information of the subject displayed by the display unit and erasure of the registered identification information of the subject remaining in the recording medium.

An information registration method according to still another aspect of the invention includes reading identification information of a subject from a recording medium which is portable and on which the identification information identifying the subject is recorded in an erasable manner; displaying the identification information of the subject read out in the reading; registering the identification information of the subject read out in the reading; and erasing the registered identification information of a subject remaining in a recording medium.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 17 is a schematic diagram of one exemplary structure of an in-vivo information acquiring system according to a fifth embodiment of the invention;

FIG. 18 is a schematic block diagram of one exemplary structure of a receiving apparatus according to the fifth embodiment;

FIG. 19 is a schematic diagram of one exemplary structure of an in-vivo information acquiring system according to a sixth embodiment of the invention;

FIG. 20 is a schematic block diagram of one exemplary structure of a receiving apparatus according to the sixth embodiment; and FIG. 21 is a schematic view of one specific example of a printed material output from a printer.

DETAILED DESCRIPTION OF THE PREFERRED EMBODIMENTS

Exemplary embodiments of a receiving apparatus and an in-vivo information acquiring system employing the receiving apparatus according to the invention will be described in detail below with reference to the accompanying drawings. The invention is not limited to the embodiments.

Figure 1:
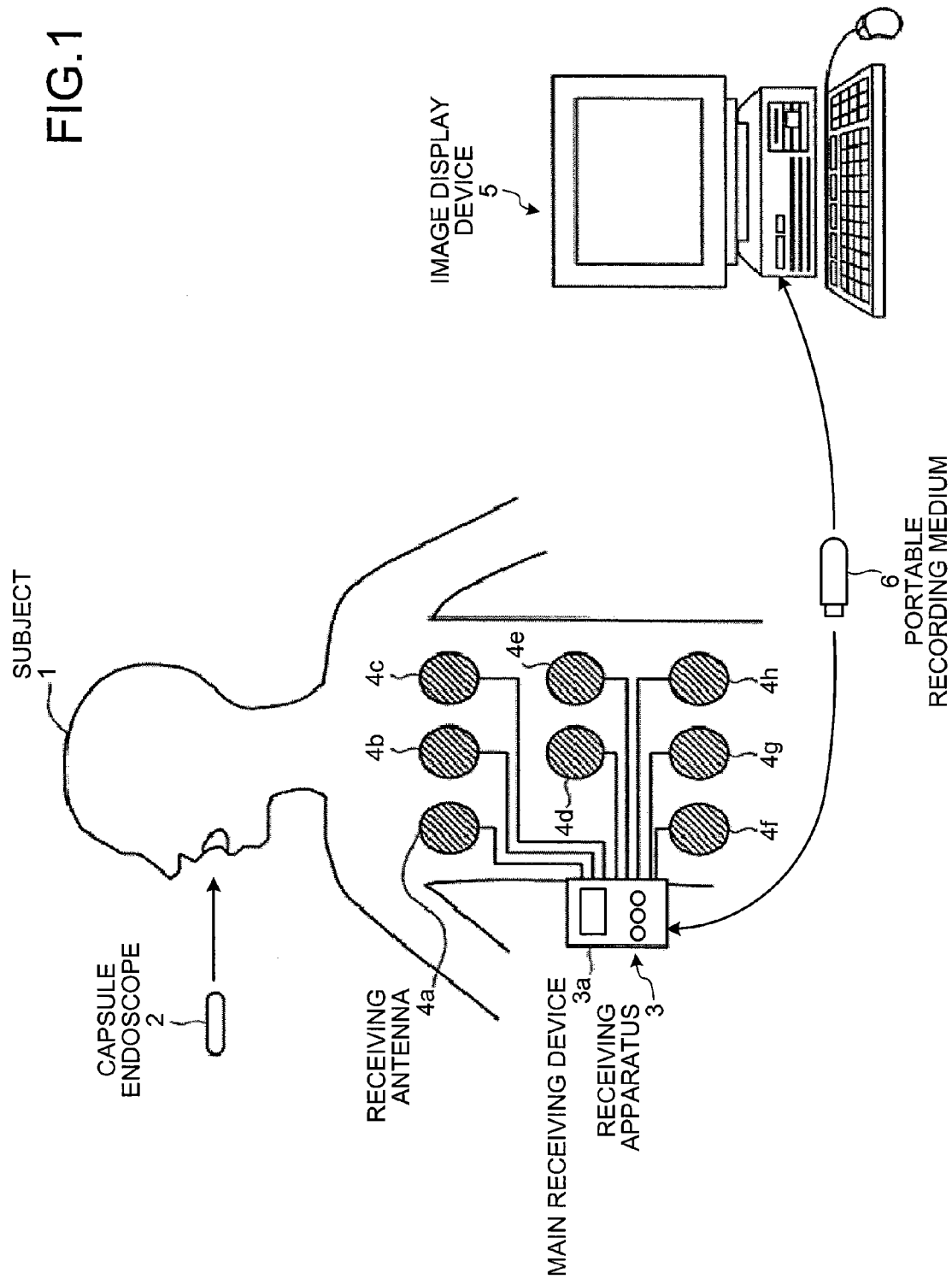
FIG. 1 is a schematic diagram of one exemplary structure of an in-vivo information acquiring system according to a first embodiment of the invention.

FIG. 1 is a schematic diagram of one exemplary structure of an in-vivo information acquiring system according to a first embodiment of the invention. As shown in FIG. 1, the in-vivo information acquiring system according to the first embodiment includes a capsule endoscope 2 which is introduced inside a subject 1 and captures images inside a digestive tract of the subject 1, a receiving apparatus 3 which receives image data acquired through image capturing by the capsule endoscope 2, an image display device 5 which displays images inside the subject 1 based on the image data acquired through image capturing by the capsule endoscope 2, and a portable recording medium 6 which serves for information delivery between the receiving apparatus 3 and the image display device 5.

The capsule endoscope 2 is introduced inside the subject, and has an imaging function of being capable of capturing images inside the subject and a radio communication function of transmitting the image data acquired through image capturing to an outside. Specifically, the capsule endoscope 2 is swallowed by the subject 1, and travels inside the digestive tract of the subject 1 following peristaltic movements. At the same time, the capsule endoscope 2 sequentially captures images inside the digestive tract of the subject 1, and sequentially transmits acquired image data of an interior of the subject 1 to the receiving apparatus 3 outside the subject 1.

The receiving apparatus 3 receives the image data acquired through image capturing by the capsule endoscope 2 and accumulates the received image data as image data of the subject which is an examination target. Specifically, the receiving apparatus 3 includes receiving antennas 4a to 4h that are arranged on a body surface of the subject, and a main receiving device 3a that receives the image data via the receiving antennas 4a to 4h. When the main receiving device 3a is attached to the subject 1, or after the main receiving device 3a is attached to the subject 1, for example, the portable recording medium 6 is connected to the main receiving device 3a in a detachable manner, and the main receiving device 3a reads out information recorded on the portable recording medium 6. Here, the main receiving device 3a performs initialization processing to set the subject 1 as an examination target based on the information read out from the portable recording medium 6. The main receiving device 3a after the initialization processing can accumulate the image data received from the capsule endoscope 2 as image data of the subject 1 as the examination target. On the other hand, the main receiving device 3a is connected to the receiving antennas 4a to 4h, for example, and receives the image data from the capsule endoscope 2 via one of the receiving antennas 4a to 4h. The main receiving device 3a receives radio signals transmitted from the capsule endoscope 2 inside the subject 1 via one of the receiving antennas 4a to 4h, and acquires image data included in the radio signals, in other words, the image data acquired through image capturing by the capsule endoscope 2. When the main receiving device 3a is initialized so that the subject 1 is recognized as the examination target, the main receiving device 3a sequentially accumulates the image data received from the pertinent capsule endoscope 2 as the image data of the subject 1.

The receiving antennas 4a to 4h are realized, for example, with a loop antenna, and arranged at predetermined positions (positions corresponding to a passage of the capsule endoscope 2, for example) on a body surface of the subject 1, as shown in FIG. 1. One of the receiving antennas 4a to 4h thus arranged in a dispersed manner on the body surface can securely receive the radio signals from the capsule endoscope 2 that travels through inside the digestive tract of the subject 1, for example, and transmits the radio signals from the capsule endoscope 2 to the main receiving device 3a. Here, one or more, or desirably plural receiving antennas may be arranged for the subject 1, and the number of the receiving antennas is not particularly limited to eight.

The image display device 5 has a structure like a workstation which displays images or the like acquired through image capturing by the capsule endoscope 2, and has processing functions for allowing the doctor or the nurse to examine the interior of the digestive tract of the subject and to make diagnosis based on the displayed images. Specifically, the image display device 5 is connected to the receiving apparatus 3 via a predetermined cradle, cable, or the like, and takes in the image data accumulated in the receiving apparatus 3, in other words, the image data acquired through image capturing by the capsule endoscope 2. The image display device 5 displays images based on the image data taken in from the receiving apparatus 3, for example, the images of the interior of the digestive tract of the subject 1. The image display device 5 may display images on a Cathode Ray Tube (CRT) display, a liquid crystal display, or the like, or alternatively, the image display device 5 may output the image to other media as in a printer. The image display device 5 may take in the image data accumulated in the receiving apparatus 3 through the portable recording medium such as a CompactFlash® that can be detachably connected to the receiving apparatus 3.

Further, the image display device 5 functions as a managing unit that manages patient information of test bodies recorded on the portable recording medium 6 in an integrated manner. Specifically, when the image display device 5 manages patient information of plural test bodies, for example, in an integrated manner, and is connected to the portable recording medium 6 via a predetermined connector or the like, the image display device 5 stores the patient information of the subject as the examination target among the patient information of the plural test bodies into the portable recording medium 6.

The portable recording medium 6 functions as a recording medium which is portable and on which the patient information is recorded, which is to be acquired by the receiving apparatus 3, of the subject as the examination target in a erasable manner. Specifically, the portable recording medium 6 is a portable recording medium such as a USB memory having a predetermined connector, and can be connected to each of the receiving apparatus 3 and the image display device 3 in a detachable manner. Here, the portable recording medium 6 is connected to the image display device 5 via a predetermined connector or the like, and the patient information of the subject is recorded on the portable recording medium 6 in such a manner that, for example, the patient information of the subject 1 among plural pieces of patient information of the plural test bodies managed in an integrated manner by the image display device 5 can be erased. The portable recording medium 6 on which the patient information of the subject 1 is recorded is connected to the receiving apparatus 3 which is to be attached to the subject 1 (in other words, the receiving apparatus 3 which receives the image data from the capsule endoscope 2 introduced inside the subject 1), and allows for the acquisition of the patient information of the subject 1 by the receiving apparatus 3. Thereafter, the patient information of the subject 1 remaining in the portable recording medium 6 is erased under the control of the receiving apparatus 3. The patient information of the subject mentioned above is identification information identifying the subject, and is, for example, a patient name, a patient ID, an age, sex, and a date of birth of the subject.

Figure 2:
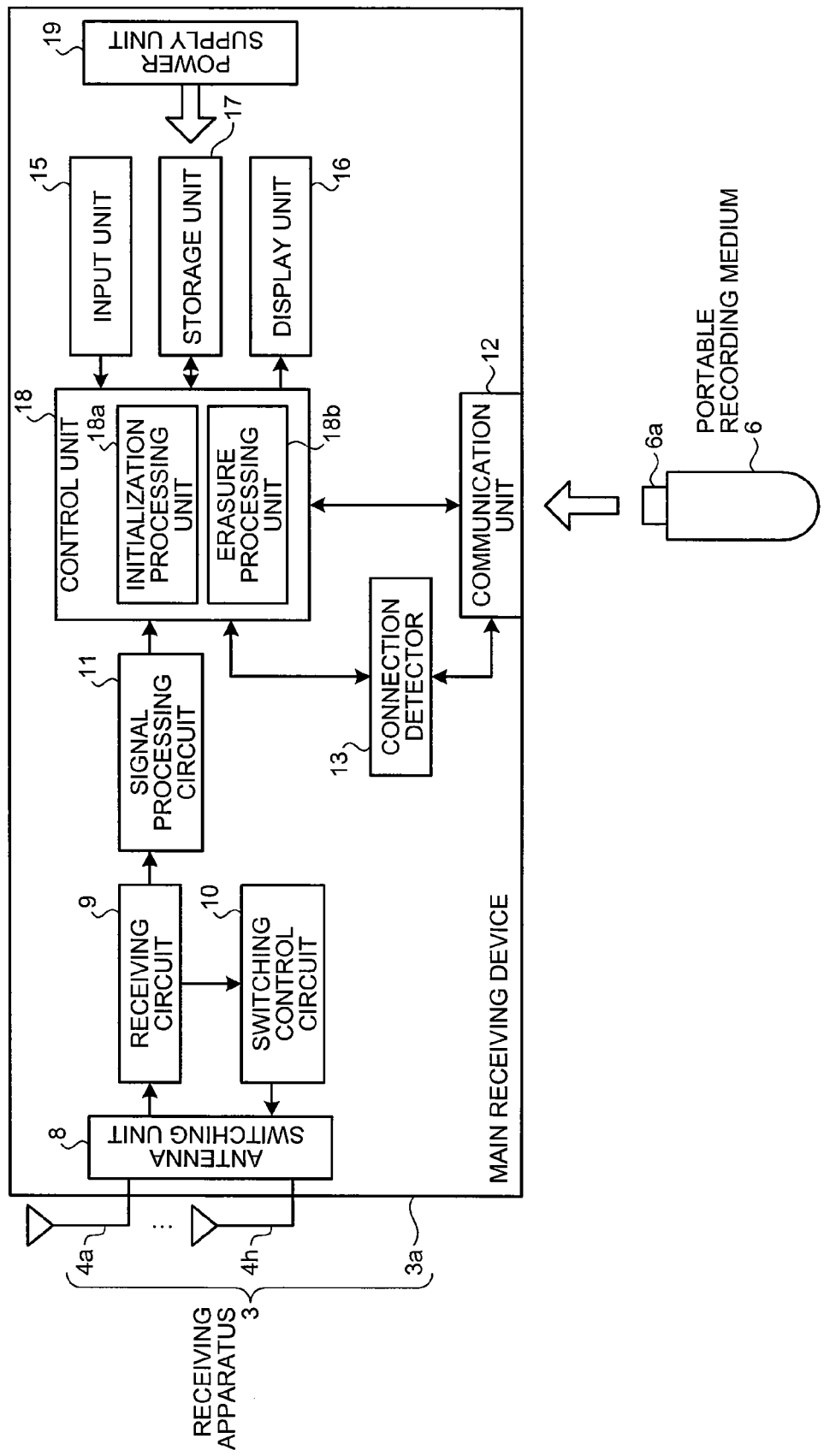
FIG. 2 is a schematic block diagram of one exemplary structure of a receiving apparatus according to the first embodiment.

Next, a structure of the receiving apparatus 3 according to the first embodiment of the invention will be described. FIG. 2 is a schematic block diagram of one exemplary structure of the receiving apparatus 3 according to the first embodiment. As shown in FIG. 2, the receiving apparatus 3 includes the receiving antennas 4a to 4h and the main receiving device 3a as mentioned above. The main receiving device 3a includes an antenna switching unit 8 which switches to one of the receiving antennas 4a to 4h as a receiving antenna to receive the radio signals from the capsule endoscope 2, a receiving circuit 9 which demodulates the radio signals received from the capsule endoscope 2 via one of the receiving antennas 4a to 4h to image signals, a switching control circuit 10 which controls an antenna switching operation of the antenna switching unit 8, and a signal processing circuit 11 which generates image data acquired by the capsule endoscope 2 based on the image signals demodulated by the receiving circuit 9. Further, the main receiving device 3a includes a communication unit 12 which transmits/receives the patient information of the subject, the image data, or the like, and a connection detector 13 which detects the connection of the portable recording medium 6 to the communication unit 12. Further, the main receiving device 3a includes an input unit 15 which receives instruction information to give instructions to a control unit 18, a display unit 16 which displays the patient information of the subject recorded on the portable recording medium 6, a storage unit 17 which accumulates various types of information such as image data, the control unit 18 which controls driving of respective elements in the receiving apparatus 3 and erasure processing of the patient information in the portable recording medium 6, and a power supply unit 19 which supplies driving power to the respective elements in the receiving apparatus 3.

The antenna switching unit 8 is connected to the receiving antennas 4a to 4h mentioned above, and performs the antenna switching operation to switch to one of the plural receiving antennas 4a to 4h as a receiving antenna to receive the radio signals from the capsule endoscope 2. The antenna switching operation of the antenna switching unit 8 is controlled by the switching control circuit 10 and the antenna switching unit 8 electrically connects one of the receiving antennas 4a to 4h to the receiving circuit 9. Here, the antenna switching unit 8 outputs the radio signals received via one of the receiving antennas 4a to 4h to the receiving circuit 9.

The receiving circuit 9 performs predetermined processing such as demodulation processing on the radio signals received via one of the receiving antennas 4a to 4h from the capsule endoscope 2, and demodulates the radio signals to the image signals. The image signals are base band signals including the image data acquired through image capturing by the capsule endoscope 2. The receiving circuit 9 outputs the resulting image signals to the signal processing circuit 11. On the other hand, the receiving circuit 9 detects field strength of the radio signal received via one of the receiving antennas 4a to 4h from the capsule endoscope 2, and generates an analog signal, for example, an RSSI (Received Signal Strength Indicator) indicating the detected received field strength. The receiving circuit 9 converts the analog signals indicating the received field strength to digital signals and outputs the resulting digital signals to the switching control circuit 10.

The switching control circuit 10 serves to control the antenna switching operation of the antenna switching unit 8 mentioned above. Specifically, the switching control circuit 10 selects a receiving antenna at which the received field strength of the radio signals from the capsule endoscope 2 is highest from the plural receiving antennas 4a to 4h based on the RSSI digital signals, for example, supplied from the receiving circuit 9, and controls the antenna switching operation of the antenna switching unit 8 so as to switch to the selected receiving antenna.

The signal processing circuit 11 serves to generate the image data included in the image signals demodulated by the receiving circuit 9. Specifically, the signal processing circuit 11 receives the image signals from the receiving circuit 9, and generates frame-based image data by performing predetermined image processing and the like on the received image signals. The image data here is the image data of the interior of the subject 1 as acquired through image capturing by the capsule endoscope 2, for example. The signal processing circuit 11 outputs the resulting image data to the control unit 18.

The communication unit 12 has a predetermined interface such as a USB connector. When the communication unit 12 is connected to a connector 6a of the portable recording medium 6, the communication unit 12 performs transmission/reception of signals between the main receiving device 3a and the portable recording medium 6. Here, the communication unit 12 functions as a reader which reads out the patient information of the subject recorded on the portable recording medium 6 connected via the connector 6a. The communication unit 12 transmits the patient information of the subject read out from the portable recording medium 6 to the control unit 18. Further, the communication unit 12 receives a control signal giving an erasure instruction of the patient information of the subject in the portable recording medium 6 from the control unit 18, and transmits the received control signal to the portable recording medium 6. The portable recording medium 6, on receiving the control signal, erases the stored patient information of the subject which is already registered. On the other hand, the communication unit 12 is connected to the image display device 5 via a predetermined cable, cradle, or the like such as a USB cable. The communication unit 12 transmits the image data supplied from the control unit 18 to the image display device 5. In other words, the image data accumulated in the main receiving device 3a is taken into the image display device 5 via the communication unit 12 and the like.

The connection detector 13 serves to detect the connection between the portable recording medium 6 and the communication unit 12. Specifically, the connection detector 13 detects the connection between the portable recording medium 6 and the communication unit 12 by detecting an electric conduction caused by the connection between the portable recording medium 6 and the communication unit 12 via the connector 6a or the like. The connection detector 13 notifies the control unit 18 of a connection detection result which indicates that the portable recording medium 6 and the communication unit 12 are connected.

The input unit 15 is realized with plural input buttons or the like, for example, and supplies instruction information or the like to give instructions to the control unit 18 in response to an input manipulation by an operator. Specifically, the input unit 15 supplies, for example, instruction information to activate the main receiving device 3a, and instruction information to start or stop a reception operation of the radio signals transmitted from the capsule endoscope 2, to the control unit 18.

The display unit 16 functions as a display unit which displays identification information of the subject in the portable recording medium 6 connected to the communication unit 12. Specifically, the display unit 16 is realized with a liquid crystal display, an organic EL (Electroluminescence) display, and the like, and displays various types of information under the control of the control unit 18. The display unit 16 displays, for example, the patient information of the subject read out from the portable recording medium 6 via the communication unit 12.

The storage unit 17 is realized with a large-capacity memory, such as an HDD (Hard Disk Drive) and a flash memory, and stores various types of information under the control of the control unit 18. The storage unit 17 stores, for example, the image data generated by the signal processing circuit 11, and the patient information of the subject registered by the control unit 18. Further, the storage unit 17 may be configured so that a portable recording medium such as a CompactFlash® and an SD memory card can be detachably attached thereto, and may sequentially accumulate the image data or the like in the attached portable recording medium.

The control unit 18 is realized with a CPU (Central Processing Unit) which executes a processing program, a ROM (Read-Only Memory) in which the processing program and the like are recorded in advance, and a RAM (Random Access Memory) in which operation parameters for each processing and various input information input to the control unit 18 and the like are stored. The control unit 18 controls driving of the respective elements in the receiving apparatus 3 based on the instruction information supplied from the input unit 15. The control unit 18 performs input/output control of the information between the respective elements. For example, the control unit 18 controls operation such as a display operation by the display unit 16, an operation to store information in the storage unit 17 or an operation to read information out of the storage unit 17, and an information transmission/reception operation of the communication unit 12. Further, the control unit 18 controls the driving of the connection detector 13, and on receiving the connection detection result indicating that the portable recording medium 6 and the communication unit 12 are connected, controls the communication unit 12 so as to read out the patient information of the subject recorded on the portable recording medium 6. The control unit 18 acquires the patient information of the subject from the portable recording medium 6 via the communication unit 12.

The control unit 18 further includes an initialization processing unit 18a which performs initialization of the main receiving device 3a based on the patient information acquired from the portable recording medium 6, and an erasure processing unit 18b which erases the patient information of the subject already registered and remaining in the portable recording medium 6. The initialization processing unit 18a, on acquiring the patient information of the subject recorded on the portable recording medium 6, performs the initialization processing to initialize the main receiving device 3a based on the patient information of the subject. In the initialization processing, the initialization processing unit 18a updates the patient information with the acquired patient information as the information identifying the subject as the examination target, and registers the acquired patient information in the main receiving device 3a. The control unit 18 stores the registered patient information of the subject in the storage unit 17. When the main receiving device 3a is thus initialized, the control unit 18 sequentially accumulates the image data from the capsule endoscope 2 as the image data of the subject identified by the registered patient information in the storage unit 17.

When the initialization processing unit 18a initializes the main receiving device 3a, the erasure processing unit 18b erases information which is the same as the patient information registered in the main receiving device 3a from the portable recording medium 6. Here, the erasure processing unit 18b generates a control signal to give an erasure instruction to erase the registered patient information remaining in the portable recording medium 6, and transmits the control signal to the portable recording medium 6 via the communication unit 12. The portable recording medium 6 erases the stored and registered patient information based on the control signal generated by the erasure processing unit 18b. Thus, the control unit 18 controls the erasure processing of the patient information in the portable recording medium 6 detachably connected to the communication unit 12.

Figure 3:
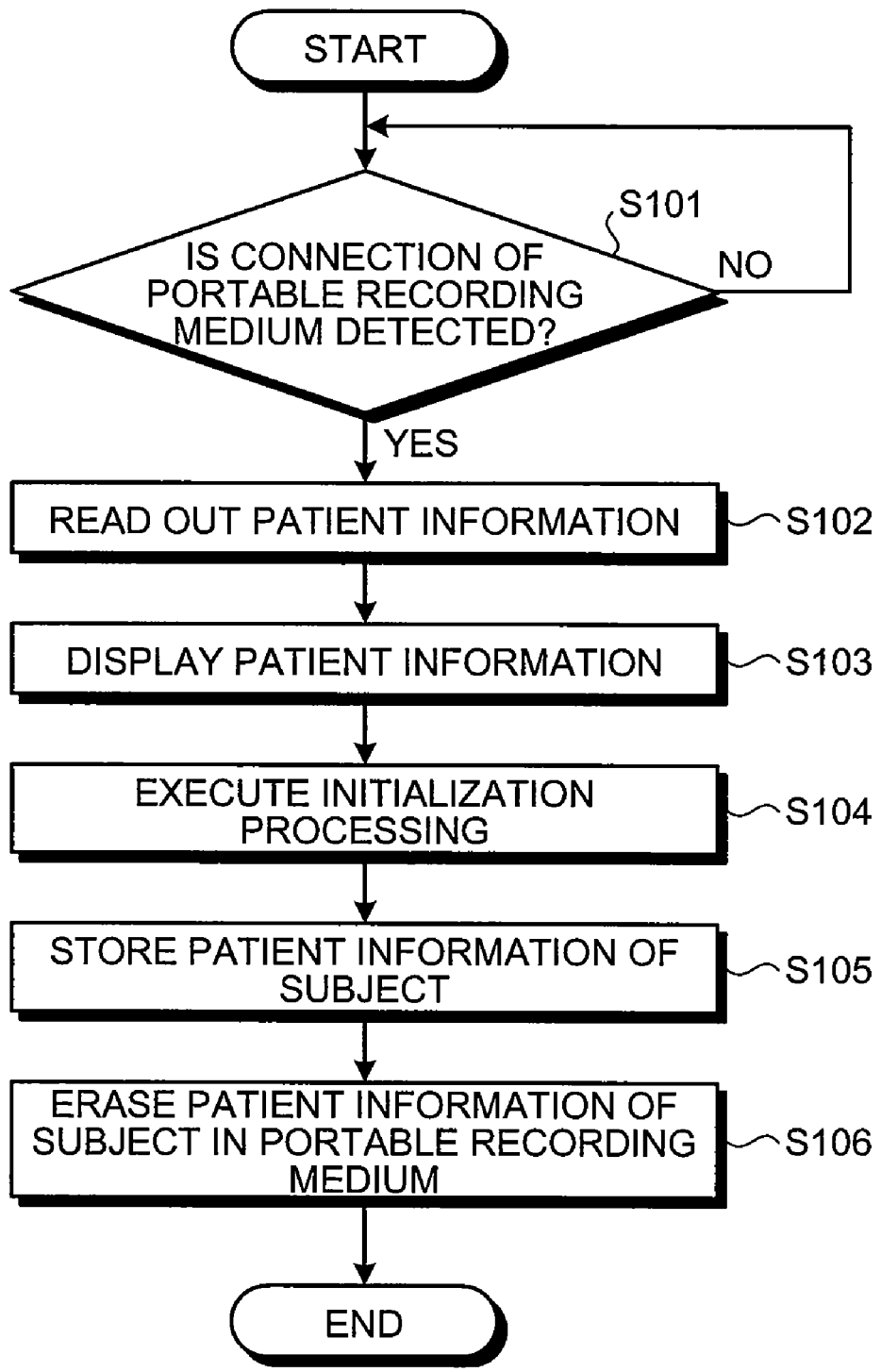
FIG. 3 is a flowchart of a processing procedure of a control unit which initializes a main receiving device and controls erasure of registered patient information in a portable recording medium.

The operation of the control unit 18 which initializes the main receiving device 3a based on the patient information recorded on the portable recording medium 6 and erases the registered patient information remaining in the portable recording medium 6 will be described. FIG. 3 is a flowchart illustrating a processing procedure of the control unit 18 performed to initialize the main receiving device 3a and to control the erasure of the registered patient information in the portable recording medium 6. In FIG. 3, the control unit 18 monitors whether the portable recording medium 6 is connected to the communication unit 12 or not on a constant basis, and when the connection between the portable recording medium 6 and the communication unit 12 is not detected (No in step S101), the control unit 18 continues monitoring whether the portable recording medium 6 and the communication unit 12 are connected or not. Here, the control unit 18 does not detect the connection between the portable recording medium 6 and the communication unit 12 unless the connection detection result indicating the connection between the portable recording medium 6 and the communication unit 12 is received from the connection detector 13.

On the other hand, the control unit 18, on receiving the connection detection result indicating the connection between the portable recording medium 6 and the communication unit 12 from the connection detector 13, detects the connection between the portable recording medium 6 and the communication unit 12 (Yes in step S101), and reads out the patient information recorded on the portable recording medium 6 (step S102). Here, the control unit 18 controls the driving of the communication unit 12 so as to read out the patient information from the portable recording medium 6, and acquires the patient information from the portable recording medium 6 via the communication unit 12.

Then, the control unit 18 displays the patient information acquired from the portable recording medium 6 on the display unit 16 (step S103), and executes the initialization processing to initialize the main receiving device 3a based on the patient information displayed on the display unit 16 (step S104). The initialization processing unit 18a updates the patient information with the patient information displayed on the display unit 16 as the information identifying the subject as the examination target (in other words, the subject to which the receiving apparatus 3 is to be attached), and thereby registers the patient information in the main receiving device 3a. The control unit 18 stores the registered patient information of the subject in the storage unit 17 (step S105).

Thereafter, the control unit 18 controls the erasure of the registered patient information remaining in the portable recording medium 6, in other words, patient information which is the same as the patient information registered in the main receiving device 3a (step S106). The erasure processing unit 18b generates a control signal to give instruction to erase the registered patient information remaining in the portable recording medium 6, and transmits the control signal to the portable recording medium 6 via the communication unit 12. The control unit 18 controls the erasure processing to erase the registered patient information remaining in the portable recording medium 6 by transmitting the control signal to the portable recording medium 6.

Figure 4:
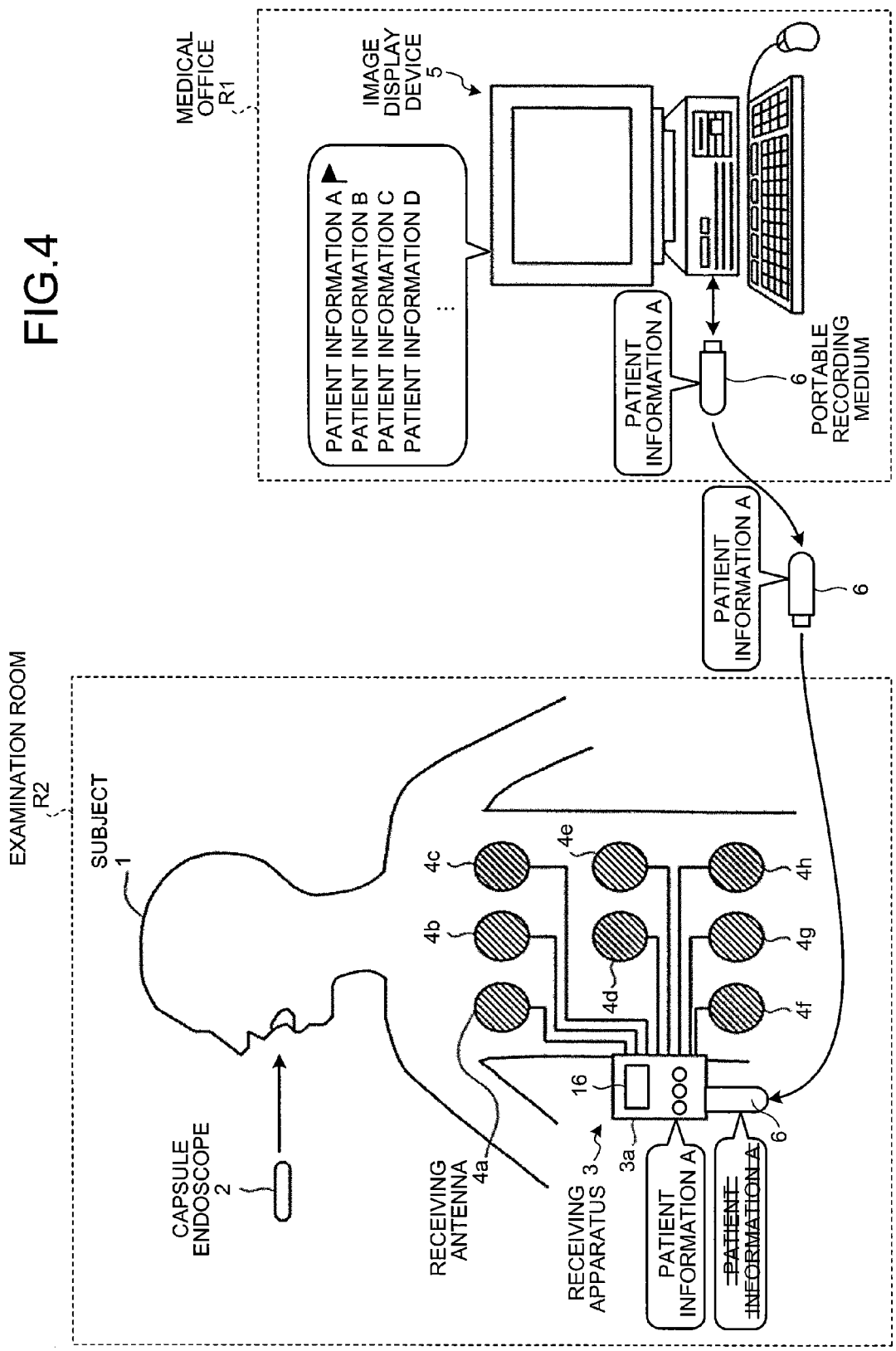
FIG. 4 is a schematic diagram illustrating how patient information which is of a subject as an examination target and recorded on the portable recording medium is registered in the receiving apparatus for the initialization of the receiving apparatus.

An effect of each element in the in-vivo information acquiring system according to the first embodiment will be specifically described based on an example where the receiving apparatus 3 is attached to the subject 1 as the examination target to which the capsule endoscope 2 is introduced. FIG. 4 is a schematic diagram illustrating how the patient information of the subject 1 as the examination target recorded on the portable recording medium 6 is registered in the receiving apparatus 3 and the receiving apparatus 3 is initialized. Hereinbelow, the effect of each element of the in-vivo information acquiring system according to the first embodiment will be described with reference to FIG. 4.

The portable recording medium 6 is detachably connected to the image display device 5 installed in a medical office R1, for example, and patient information A of the subject 1 as the examination target is recorded on the portable recording medium 6 in an erasable manner. Specifically, the image display device 5 manages the patient information (patient information A, B, C, D, . . . ) of plural test bodies including the patient information A in an integrated manner. When connected to the portable recording medium 6 via a connector or the like in a detachable manner, the image display device 5 writes copy information of the patient information A of the subject 1 selected from the patient information of the plural test bodies into the portable recording medium 6. The patient information A of the subject 1 is recorded on the portable recording medium 6 in an erasable manner. The image display device 5 selects the patient information to be written into the portable recording medium 6 from the patient information of the plural test bodies according to a selection manipulation of the patient information performed by an examiner such as a doctor and a nurse.

Further, when the patient information A is written into the portable recording medium 6, for example, the image display device 5 affixes a flag indicating that the portable recording medium 6 takes out the patient information A to the patient information A (in other words, original patient information A managed in an integrated manner). The image display device 5 manages the patient information of the plural test bodies in an integrated manner as described above, and also manages whether each of the patient information is taken out by the portable recording medium or the like or not.

On the other hand, the portable recording medium 6 on which the patient information A of the subject 1 is recorded in an erasable manner is taken into an examination room R2 where the subject 1 waits. To the subject 1 waiting in the examination room R2, the receiving apparatus 3 which is to accumulate the image data acquired through image capturing by the capsule endoscope 2 is attached. Here, the receiving antennas 4a to 4h are arranged on a body surface of the subject 1 in a dispersed manner, and the main receiving device 3a to which the receiving antennas 4a to 4h are connected is attached to a torso of the subject 1, for example. When the receiving apparatus 3 is attached to the subject 1, the receiving apparatus 3 is uniquely determined as an apparatus for accumulating the image data of the subject 1. The receiving apparatus 3 which is attached to the subject 1 is the one on which a predetermined operation check has been performed in advance, and is in a state where the radio signals including the image data acquired through image capturing by the capsule endoscope 2 are correctly received after the capsule endoscope 2 is introduced into the subject 1 until discharged outside the body.

The portable recording medium 6 on which the patient information A of the subject 1 is recorded in an erasable manner is detachably connected to the receiving apparatus 3 which is attached to the subject 1. Specifically, the portable recording medium 6 is detachably connected to the main receiving device 3a of the receiving apparatus 3 when the receiving apparatus 3 is attached to the subject 1 or after the receiving apparatus 3 is attached to the subject 1. The control unit 18 of the main receiving device 3a follows the processing procedure of steps S101 to S106 mentioned above. Specifically, the control unit 18 reads out the patient information A recorded on the portable recording medium 6 and displays the same on the display unit 16. Thereafter, the control unit 18 updates the patient information of the subject 1 as the examination target with the displayed patient information A, and registers the patient information A in the main receiving device 3a. The examiner can easily confirm whether the patient information registered in the main receiving device 3a matches with the subject 1 as the examination target, by visually confirming the patient information A displayed on the display unit 16. Further, the control unit 18 stores the patient information A in the storage unit 17, and controls the erasure processing to erase the registered patient information A remaining in the portable recording medium 6. The portable recording medium 6, under the control of the control unit 18, erases the remaining and registered patient information A. Thereafter, the portable recording medium 6 from which the registered patient information A is erased is removed from the main receiving device 3a.

Since the receiving apparatus 3 is uniquely determined with respect to the subject 1 as the examination target, and the patient information A of the subject 1 is registered in the main receiving device 3a of the receiving apparatus 3, the main receiving device 3a can securely be initialized so that the image data received from the capsule endoscope 2 is accumulated as the image data of the subject 1. Further, since the patient information registered in the main receiving device 3a is displayed on the display unit 16, the examiner can securely register the patient information A of the subject 1 as the examination target in the main receiving device 3a without mistaking the subject 1 as the examination target for another subject.

The main receiving device 3a which is initialized based on the patient information A accumulates the image data received from the capsule endoscope 2 as the image data of the subject 1. As mentioned above, the main receiving device 3a is attached to the subject 1 which is identified by the patient information A and is uniquely determined with respect to the subject 1. Therefore, when the capsule endoscope 2 is introduced into the subject 1, the main receiving device 3a does not mistake the subject 1 as the examination target for another subject and can correctly accumulate the image data acquired through image capturing by the capsule endoscope 2 as the image data of the subject 1.

Thereafter, the image data of the subject 1 accumulated in the main receiving device 3a is taken into the image display device 5 in the medical office R1 mentioned above via the main receiving device 3a or the portable recording medium. The image display device 5 acquires the patient information A of the subject 1 together with the image data of the subject 1, and recognizes that the patient information A which is taken out by the portable recording medium 6 is returned together with the image data. When the image display device 5 recognizes that the patient information A is returned, the image display device 5 deletes the flag affixed to the original patient information A under the integrated management. On the other hand, the image display device 5 displays the image of the interior of the digestive tract of the subject 1 based on the acquired image data of the subject 1. The examiner observes (examines) the image of the interior of the digestive tract of the subject 1 displayed on the image display device 5 and makes diagnosis of the subject 1.

In the first embodiment of the invention, the control unit 18 displays the patient information acquired from the portable recording medium 6 on the display unit 16 and registers the same, though the invention is not limited thereto; and the control unit 18 may display the patient information acquired from the portable recording medium 6 on the display unit 16 first, and later register the patient information only when the instruction information instructing to register the displayed patient information is supplied from the input unit 15.

The control unit 18 displays the patient information acquired from the portable recording medium 6 on the display unit 16, though the invention is not limited thereto; and the patient information acquired from the portable recording medium 6 may be displayed on the display unit 16 followed by the display of the registered patient information on the display unit 16. The examiner can confirm whether the patient information of the subject as the examination target is correctly registered in the main receiving device 3a or not by visually confirming the registered patient information displayed on the display unit 16.

In the first embodiment of the invention, the patient information of one subject is recorded on the portable recording medium 6 in an erasable manner, though the invention is not limited thereto; and the patient information of plural test bodies may be recorded on the portable recording medium 6 in an erasable manner. The control unit 18 acquires the patient information of the plural test bodies recorded on the portable recording medium 6 and displays a list of the patient information of the plural test bodies on the display unit 16. The control unit 18 further selects the patient information of a desirable subject from the patient information of the plural test bodies based on the instruction information supplied from the input unit 15, and registers the selected patient information of the subject. Thereafter, the control unit 18 erases the registered patient information of the subject from the patient information of the plural test bodies remaining in the portable recording medium 6.

As described above, in the first embodiment of the invention, the patient information of the subject is acquired and displayed with the use of the portable recording medium on which the patient information identifying the subject as the examination target is recorded in an erasable manner, the displayed patient information of the subject is registered in the main receiving device, and the registered patient information remaining in the portable recording medium is erased. Therefore, the patient information of the subject can be registered in the main receiving device which is uniquely determined with respect to the subject, and the main receiving device can be securely initialized so that the image data received from the capsule endoscope is accumulated as the image data of the subject. Thus, the receiving apparatus which can prevent the subject as the examination target from being mistaken for another subject, and correctly acquire the image data acquired through image capturing by the capsule endoscope as the image data of the subject as the examination target, and the in-vivo information acquiring system employing the same can be realized.

Further, the structure is made so that the patient information acquired from the portable recording medium is displayed. Therefore, the examiner can easily confirm whether the patient information registered in the main receiving device matches with the subject as the examination target to which the main receiving device is attached. Thus, the patient information of the subject as the examination target can be securely registered in the main receiving device of the receiving apparatus of the invention without the subject of the examination target being mistaken for the other subject.

Further, since the main receiving device is attached to the subject after the main receiving device is confirmed to be in a state where the image data transmitted from the capsule endoscope is correctly received, and the patient information of the subject can be registered in the main receiving device, the image data from the capsule endoscope can be sequentially accumulated in the main receiving device immediately after the initialization of the main receiving device. Therefore, a state, in which the main receiving device does not operate normally at an introduction of the capsule endoscope into the subject or after the introduction, can be prevented, and time and efforts required for preparatory works before the image data from the capsule endoscope introduced inside the subject is accumulated in the main receiving device can be reduced.

A second embodiment of the invention will be described. In the first embodiment described above, the display unit 16 which displays the patient information recorded on the portable recording medium 6 is incorporated in the main receiving device 3a in an integral manner. In the second embodiment, an external monitor which displays a list of patient information recorded on the portable recording medium 6 is detachably attached to the main receiving device, and the patient information to be registered in the main receiving device is selected from the list of patient information displayed on the external monitor.

Figure 5:
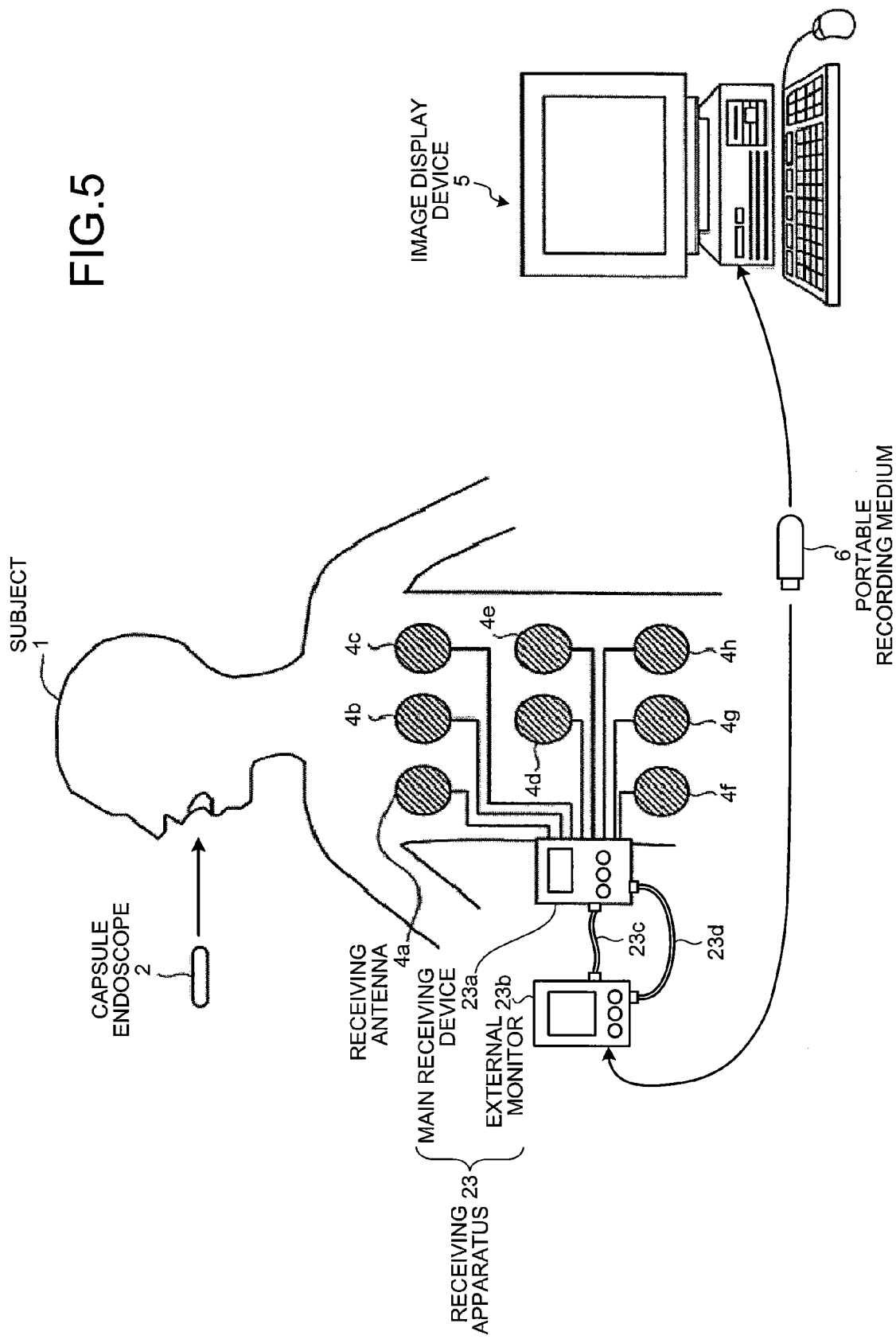
FIG. 5 is a schematic diagram of one exemplary structure of an in-vivo information acquiring system according to a second embodiment of the invention.

FIG. 5 is a schematic diagram of an exemplary structure of an in-vivo information acquiring system according to the second embodiment of the invention. As shown in FIG. 5, the in-vivo information acquiring system according to the second embodiment includes a receiving apparatus 23 in place of the receiving apparatus 3 of the in-vivo information acquiring system according to the first embodiment mentioned above. In other respects, the structure of the in-vivo information acquiring system according to the second embodiment is the same as the structure of the first embodiment, and the same elements are denoted by the same reference characters.

The receiving apparatus 23 includes a main receiving device 23a to which the aforementioned receiving antennas 4a to 4h are connected, and an external monitor 23b which is detachably connected to the main receiving device 23a via cables 23c and 23d, for example. The main receiving apparatus 23a receives the patient information from the external monitor 23b via the cable 23d and initializes based on the received patient information. Then, the main receiving device 23a becomes able to sequentially accumulate the image data of the subject identified by the patient information. Further, the main receiving device 23a, similarly to the main receiving device 3a of the receiving apparatus 3 according to the first embodiment described above, is attached to the subject 1 as the examination target, receives the radio signals from the capsule endoscope 2 via one of the receiving antennas 4a to 4h, and sequentially accumulates the image data included in the radio signals, i.e., the image data acquired through image capturing by the capsule endoscope 2.

The external monitor 23b receives the image data received by the main receiving device 23a from the capsule endoscope 2 via the cable 23c, and displays images based on the image data on a screen. Further, the external monitor 23b functions as an external display which displays one or more pieces of the patient information recorded on the portable recording medium 6. Specifically, the external monitor 23b is detachably connected to the portable recording medium 6 on which the patient information of plural test bodies is recorded in an erasable manner, for example, reads out the patient information of the plural test bodies recorded on the portable recording medium 6, and displays a list of the patient information of the plural test bodies in the portable recording medium 6. Here, the external monitor 23b transmits the patient information of the subject selected from the patient information of the plural test bodies displayed as the list to the main receiving device 23a. Thereafter, the external monitor 23b erases the registered patient information of the subject in the portable recording medium 6 based on the instruction-of the main receiving device 23a.

Figure 6:
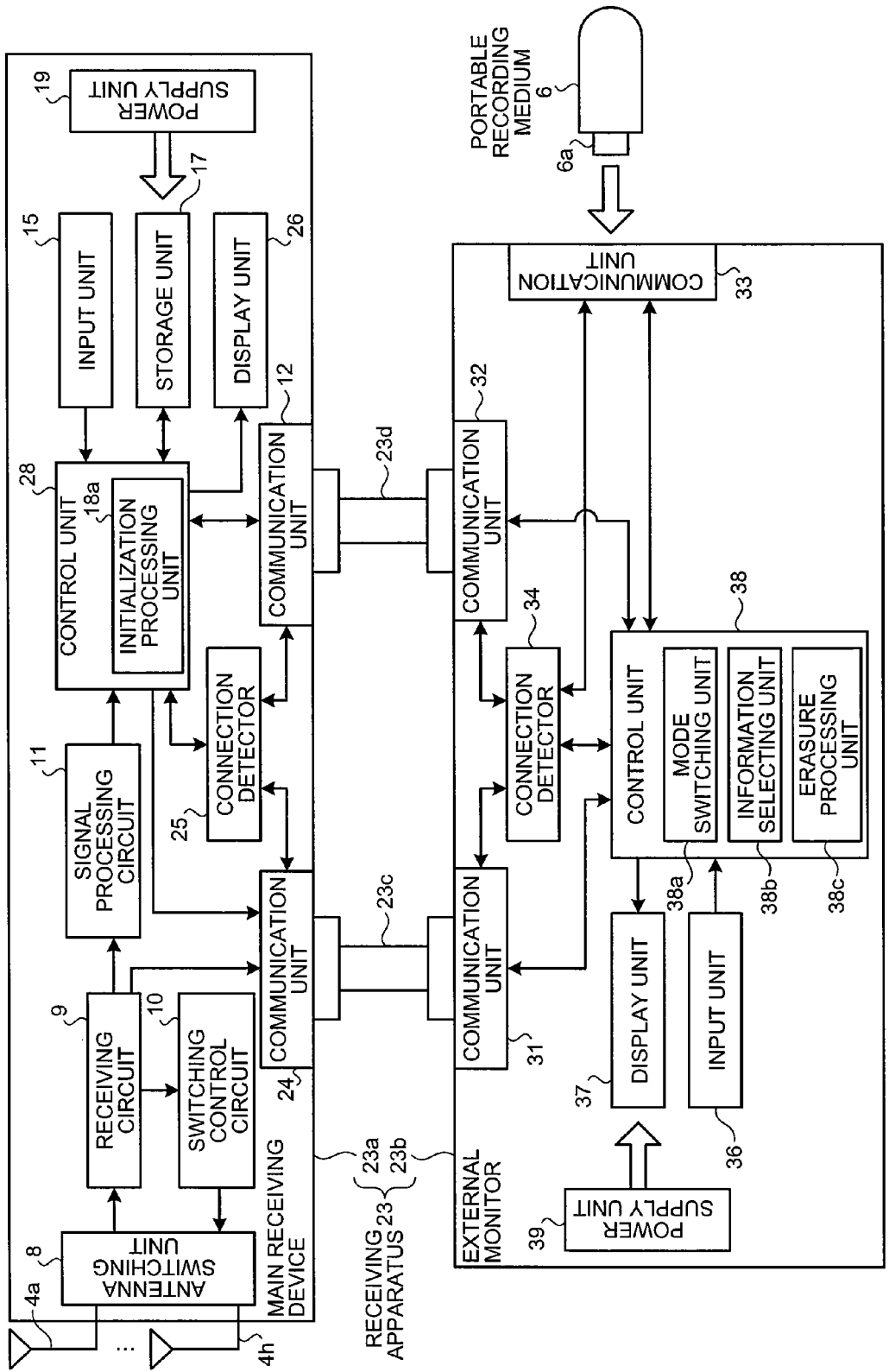
FIG. 6 is a schematic block diagram of one exemplary structure of a receiving apparatus according to the second embodiment.

A structure of the receiving apparatus 23 according to the second embodiment of the invention will be described. FIG. 6 is a schematic block diagram of an exemplary structure of the receiving apparatus 23 according to the second embodiment. As shown in FIG. 6, the main receiving device 23a of the receiving apparatus 23 includes a connection detector 25 in place of the connection detector 13 of the main receiving device 3a of the receiving apparatus 3 according to the first embodiment, a display unit 26 in place of the display unit 16, and a control unit 28 in place of the control unit 18. Further, the main receiving device 23a further includes a communication unit 24 and is detachably connected to the external monitor 23b via the cables 23c and 23d. The portable recording medium 6 is detachably connected to the external monitor 23b. In other respects, the structure of the second embodiment is the same as the structure of the first embodiment, and the same elements are denoted by the same reference characters.

The cables 23c and 23d are, for example, cables for serial communication, and has a predetermined interface such as a USB connector. Specifically, the cable 23c can be detachably attached to the communication unit 24 of the main receiving device 23a and a communication unit 31 of the external monitor 23b, and communicatively connects the communication unit 24 and the communication unit 31. On the other hand, the cable 23d can be detachably connected to the communication unit 12 of the main receiving device 23a and a communication unit 32 of the external monitor 23b, and communicatively connects the communication unit 12 and the communication unit 32.

The communication unit 24 has an interface which is detachably connected to the cable 23c, and transmits the image data to the external monitor 23b via the cable 23c. Specifically, the communication unit 24 receives the image signal demodulated by the receiving circuit 9, and transmits the image signal in series to the external monitor 23b via the cable 23c. The image signal includes image data acquired through image capturing by the capsule endoscope 2.

The connection detector 25 detects that the communication unit 24 and the external monitor 23b are connected via the cable 23c by detecting an electric conduction caused by the connection between the communication unit 24 and the external monitor 23b via the cable 23c. On detecting the connection between the communication unit 24 and the external monitor 23b, the connection detector 25 transmits the connection detection result indicating the connection between the communication unit 24 and the external monitor 23b to the control unit 28. On the other hand, the connection detector 25 detects that the communication unit 12 and the external monitor 23b are connected via the cable 23d by detecting an electric conduction caused by the connection between the communication unit 12 and the external monitor 23b via the cable 23d. On detecting the connection between the communication unit 12 and the external monitor 23b, the connection detector 25 transmits the connection detection result indicating the connection between the communication unit 12 and the external monitor 23b to the control unit 28.

The display unit 26 serves to display the patient information, registered in the main receiving device 23a, of the subject. Specifically, the display unit 26 is realized with a liquid crystal display, an organic EL display, or the like, and displays the registered patient information of the subject under the control of the control unit 28. In other words, the display unit 26 can present the patient information currently registered in the main receiving device 23a to the examiner and the like.

The control unit 28 has substantially the same function and the structure as those of the control unit 18 of the main receiving device 3a of the first embodiment described earlier, and controls the driving of the respective elements in the main receiving device 23a. The control unit 28, similarly to the control unit 18 mentioned above, performs an input/output control of information between the respective elements, for example, controls the display operation by the display unit 26, the operation to store information in the storage unit 17 or the operation to read out information of the storage unit 17, and the information transmission/reception operation of the communication units 12 and 24. Further, the control unit 28 controls the driving of the connection detector 25, and receives the detection result on the connection between the communication unit 24 and the external monitor 23b and the detection result on the connection between the communication unit 12 and the external monitor 23b from the connection detector 25. On receiving the connection detection result indicating the connection between the communication unit 24 and the external monitor 23b, the control unit 28 controls the communication unit 24 so as to transmit the image signal demodulated by the receiving circuit 9 to the external monitor 23b. Further, on receiving the connection detection result indicating the connection between the communication unit 12 and the external monitor 23b, the control unit 28 controls the communication unit 12 so as to transmit/receive various types of information such as the patient information of the subject between the main receiving device 23a and the external monitor 23b.

Further, the control unit 28 has the initialization processing unit 18a described earlier. The initialization processing unit 18a performs the initialization processing to initialize the main receiving device 23a based on the patient information of the subject acquired from the external monitor 23b via the cable 23d. The control unit 28 stores the patient information (registered patient information of the subject) registered in the main receiving device 23a in the initialization processing in the storage unit 17.

When the main receiving device 23a is initialized as described above, the control unit 28, similarly to the control unit 18 of the main receiving device 3a mentioned earlier, sequentially accumulates the image data from the capsule endoscope 2 as the image data of the subject identified by the registered patient information in the storage unit 17. Further, when the main receiving device 23a is initialized, the control unit 28 transmits the instruction information to instruct the erasure processing of the registered patient information (hereinafter referred to as the erasure instruction information) to the external monitor 23b via the communication unit 12. The control unit 28 transmits the erasure instruction information to the external monitor 23b to control the external monitor 23b so as to erase the registered patient information of the subject remaining in the portable recording medium 6 connected to the external monitor 23b. The control unit 28 controls the erasure processing of the portable recording medium 6 via the control of the external monitor 23b.

The erasure instruction information can be any information which can be a trigger of the erasure processing according to which the registered patient information of the subject remaining in the portable recording medium 6 is erased by the external monitor 23b, and for example, the erasure instruction information may be information instructing the erasure of the registered patient information of the subject, or information notifying the external monitor 23b that the initialization of the main receiving device 23a has finished.

On the other hand, the external monitor 23b of the receiving apparatus 23, as shown in FIG. 6, includes the communication unit 31 which serves to receive the image signal from the main receiving device 23a via the cable 23c, the communication unit 32 which transmits/receives the patient information of the subject or the erasure instruction information via the cable 23d, and a communication unit 33 which performs transmission/reception of information between the portable recording medium 6 and the external monitor 23b. Further, the external monitor 23b includes a connection detector 34 which detects connection between the main receiving device 23a and each of the communication units 31 and 32, and connection between the portable recording medium 6 and the communication unit 33, an input unit 36 which receives instruction information to give instructions to a control unit 38, and a display unit 37 which displays the image acquired through image capturing by the capsule endoscope 2 and the patient information recorded on the portable recording medium 6. Further, the external monitor 23b includes the control unit 38 which controls the driving of the respective elements in the external monitor 23b, and a power supply unit 38 which supplies driving power to the respective elements in the external monitor 23b.

The communication unit 31 has an interface to detachably connect to the cable 23c, and receives the image data from the main receiving device 23a via the cable 23c. Specifically, the communication unit 31 is communicatively connected to the communication unit 24 of the main receiving device 23a via the cable 23c, and receives the image signals transmitted by the communication unit 24. The communication unit 31 transmits the image signals to the control unit 38. The image signals here include image data acquired through image capturing by the capsule endoscope 2.

The communication unit 32 has an interface to detachably connect to the cable 23d, and is communicatively connected to the communication unit 12 of the main receiving device 23a via the cable 23d. The communication unit 32 transmits the patient information of the subject, whose transmission is instructed by the control unit 38, to the communication unit 12, and allows for the acquisition of the patient information of the subject by the control unit 28. Further, the communication unit 32 receives the erasure instruction information from the control unit 28 via the communication unit 12 and transmits the erasure instruction information to the control unit 38.

The communication unit 33 has a predetermined interface such as an USB connector, and performs transmission/reception of signals between the external monitor 23b and the portable recording medium 6 when the connector 6a of the portable recording medium 6 is connected. Here, the communication unit 33 functions as a reader which reads out the patient information of the subject recorded on the portable recording medium 6 connected via the connector 6a. The communication unit 33 transmits the patient information of the subject read out from the portable recording medium 6 to the control unit 38. Further, the communication unit 33 receives a control signal giving the erasure instruction of the patient information of the subject in the portable recording medium 6 from the control unit 38, and transmits the received control signal to the portable recording medium 6. On receiving the control signal, the portable recording medium 6 erases the stored and registered patient information of the subject.

The connection detector 34 detects that the communication unit 24 and the communication unit 31 are connected via the cable 23c by detecting an electric conduction caused by the connection between the communication unit 24 and the communication unit 31 via the cable 23c. Similarly, the connection detector 34 detects that the communication unit 12 and the communication unit 32 are connected via the cable 23d by detecting an electric conduction caused by the connection between the communication unit 12 and the communication unit 32 via the cable 23d. Further, the connection detector 34 detects that the portable recording medium 6 and the communication unit 33 are connected by detecting an electric conduction caused by the connection between the portable recording medium 6 and the communication unit 33 via the connector 6a and the like. On detecting the connection between the communication unit 24 and the communication unit 31 via the cable 23c, the connection detector 34 transmits the connection detection result indicating that the communication unit 24 and the communication unit 31 are connected to the control unit 38, whereas on detecting the connection between the communication unit 12 and the communication unit 32 via the cable 23d, the connection detector 34 transmits the connection detection result indicating that the communication unit 12 and the communication unit 32 are connected to the control unit 38. Further, on detecting the connection between the portable recording medium 6 and the communication unit 33 via the connector 6a and the like, the connection detector 34 transmits the connection detection result indicating that the potable recording medium 6 and the communication unit 33 are connected to the control unit 38.

The input unit 36 is realized, for example, with plural input buttons, and the like, and receives instruction information to give instructions to the control unit 38 in response to the input manipulation by the operator, for example. The input unit 36 inputs, for example, the instruction information to activate the external monitor 23b, the instruction information to give instructions on a control mode of the control unit 38, and the instruction information to designate the patient information of the subject to be transmitted to the main receiving device 23a, to the control unit 38.

The display unit 37 displays a list of identification information of one or more test bodies read out from the portable recording medium 6 under the control of the control unit 38, or, displays an image based on the image data received from the main receiving device 23a (in other words, an image captured by the capsule endoscope 2) on the monitor. Specifically, the display unit 37 is realized with a liquid crystal display, an organic EL display, or the like, and displays various types of information under the control of the control unit 38. For example, the display unit 37 displays an image acquired through image capturing by the capsule endoscope 2 based on the image data input from the control unit 38 on the monitor. Further, the display unit 37 displays a list of patient information of one or more test bodies in the portable recording medium 6 based on one or more pieces of patient information input from the control unit 38. The examiner can confirm the image data received by the main receiving device 23a from the capsule endoscope 2, or can select the patient information of the subject as the examination target from the one or more pieces of patient information in the portable recording medium 6, by visually confirming the display on the monitor of the display unit 37.

The control unit 38 is realized with a CPU (Central Processing Unit) which executes a processing program, a ROM in which the processing program or the like are recorded in advance, and a RAM in which operation parameters of each processing and various pieces of input information input from the control unit 18 are recorded. The control unit 38 controls the driving of the respective elements in the receiving apparatus 3 based on the instruction information input from the input unit 36. Specifically, the control unit 38 performs an input/output control of information between the respective elements, for example, the control unit 38 controls the display operation by the display unit 16, and the information transmission/reception operation of each of the communication units 31 to 33. Further, the control unit 38 controls the driving of the connection detector 34, and controls the communication unit 33 so as to read out the patient information of the subject recorded on the portable recording medium 6 on receiving the connection detection result indicating that the portable recording medium 6 and the communication unit 33 are connected from the connection detector 34. The control unit 38, then, acquires the patient information of one or more test bodies from the portable recording medium 6 via the communication unit 33. On the other hand, on receiving the connection detection result indicating that the communication unit 24 is connected to the communication unit 31 via the cable 23c from the connection detector 34, the control unit 38 receives the image signals via the communication unit 31 and generates the image data by performing predetermined image processing on the image signals. The control unit 38 transmits thus generated image data to the display unit 37 and displays the image based on the image data on the display unit 37.

Further, the control unit 38 includes a mode switching unit 38a which switches the control mode to an image display mode or an initialization mode, an information selecting unit 38b which selects the patient information to be transmitted to the main receiving device 23a from one or more patient information displayed as a list on the display unit 37, and an erasure processing unit 38c which erases the registered patient information of the subject in the portable recording medium 6 based on the erasure instruction from the main receiving device 23a. The mode switching unit 38a switches the control mode to the image display mode or the initialization mode based on mode designating information input from the input unit 36. The image display mode is a control mode in which the image acquired through image capturing by the capsule endoscope 2 is displayed on the display unit 37. On the other hand, the initialization mode is a control mode in which the patient information of the subject is displayed on the display unit 37 for the initialization of the main receiving device 23a, and the main receiving device 23a acquires the patient information of the subject.

The information selecting unit 38b selects the patient information to be acquired by the main receiving device 23a from the patient information of one or more test bodies displayed as a list on the display unit 37 based on selection instruction information input from the input unit 36. The selection instruction information is instruction information input to the control unit 38 in response to the input manipulation by the operator on the input unit 36, and is instruction information to give a selection instruction of the patient information of a desirable subject from the patient information of one or more test bodies displayed as a list on the display unit 37. The control unit 38 controls the communication unit 32 so as to transmit the patient information of the subject selected by the information selecting unit 38b to the main receiving device 23a.

The erasure processing unit 38c erases the registered patient information of the subject in the portable recording medium 6 based on the erasure instruction from the control unit 28 of the main receiving device 23a. Specifically, the control unit 38 receives the erasure instruction information mentioned above from the control unit 28 via the communication unit 32. The erasure processing unit 38c generates a control signal to give the erasure instruction of the registered patient information remaining in the portable recording medium 6 based on the erasure instruction information and transmits the control signal to the portable recording medium 6 via the communication unit 33. Then, the portable recording medium 6 performs erasure processing to erase the stored and registered patient information based on the control signal.

Figure 7:
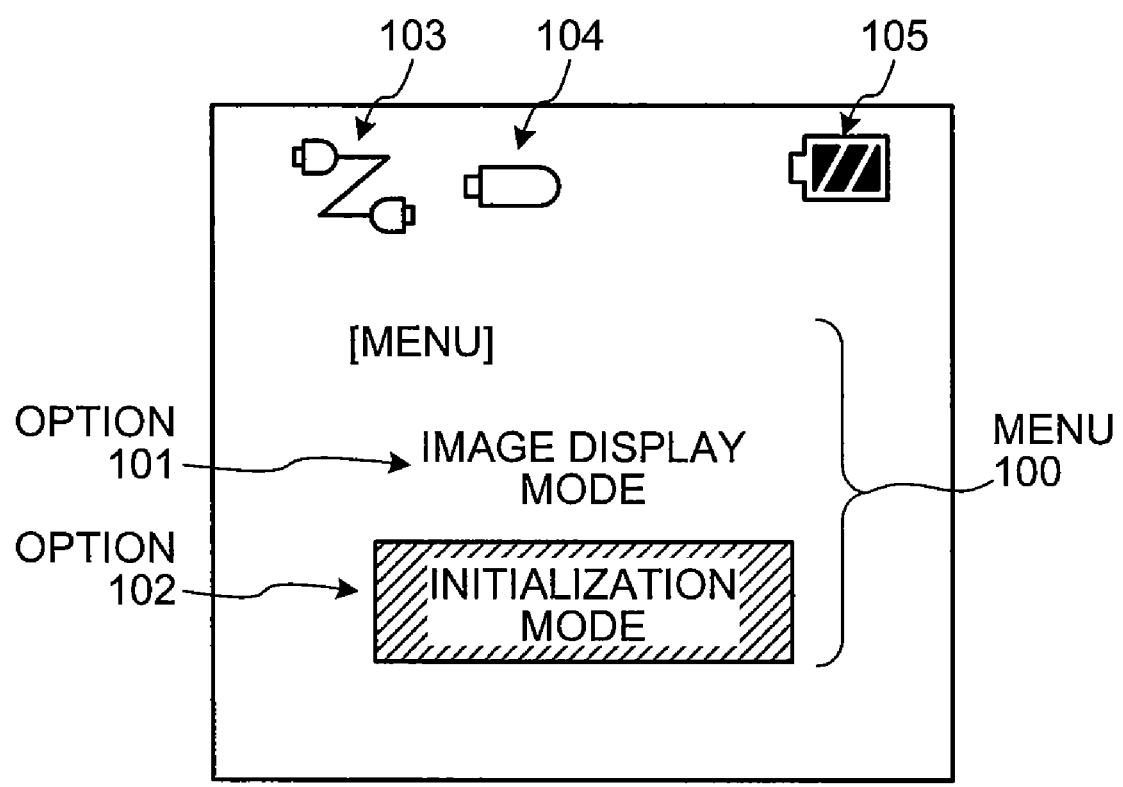
FIG. 7 is a schematic diagram of one specific example of a menu screen which is employed for selection of a control mode of a control unit.

An operation of the control unit 38 performed to switch the control mode to the image display mode or the initialization mode by the mode switching unit 38a will be described. FIG. 7 is a schematic diagram of one specific example of a menu screen employed for the selection of the control mode of the control unit 38.

Firstly, the control unit 38 displays a menu 100 for the selection of the control mode as shown in FIG. 7 on the display unit 37, for example. When the control unit 38 receives the connection detection result indicating that the communication unit 24 and the communication unit 31 are connected, the control unit 38 displays a connection mark 103 indicating that the communication unit 24 and the communication unit 31 are in a connected state, as well as an option 101 employed for selection of the image display mode in the menu 100. Further, when the control unit 38 receives the connection detection result indicating that the communication unit 12 and the communication unit 32 are connected and the connection detection result indicating that the portable recording medium 6 and the communication unit 33 are connected, the control unit 38 displays a connection mark 104 indicating that the communication unit 12 and the communication unit 32 are in a connected state and the portable recording medium 6 and the communication unit 33 are in a connected state, and at the same time, the control unit 38 displays an option 102 for selection of the initialization mode in the menu 100. Further, the control unit 38 displays a remaining power amount mark 105 indicating the remaining amount of driving power in the power supply unit 39 on the display unit 37.

The input unit 36, in response to the input manipulation giving a selection instruction of one of the options 101 and 102 on the menu 100, inputs mode designating information giving a selection instruction of the image display mode or mode designating information giving a selection instruction of the initialization mode to the control unit 38. Specifically, the input unit 36 inputs the mode designating information giving the selection instruction of the image display mode to the control unit 38 when the operator selects the option 101, whereas the input unit 36 inputs the mode designating information giving the selection instruction of the initialization mode to the control unit 38 when the operator selects the option 102.

The control unit 38 receives the mode designating information as described above from the input unit 36 and switches the control mode to one of the image display mode and the initialization mode based on the acquired mode designating information. Here, the mode switching unit 38a switches the control mode to the image display mode based on the mode designating information giving the selection instruction of the image display mode, or switches the control mode to the initialization mode based on the mode designating information giving the selection instruction of the initialization mode.

The control unit 38 whose control mode is set to the image display mode receives the image signals from the main receiving device 23a via the communication unit 31, generates the image data based on the image signals, and displays the image based on the image data (in other words, the image acquired through image capturing by the capsule endoscope 2) on the display unit 37. The control unit 38 displays the menu 100 again on the display unit 37 when the display of a series of images acquired from the capsule endoscope 2 by the main receiving device 23a on the display unit 37 is finished.

On the other hand, when the control unit 38 is set to the initialization mode, the control unit 38 displays a list of the patient information of one or more test bodies read out from the portable recording medium 6 via the communication unit 33 on the display unit 37, selects the patient information of the subject to be registered in the main receiving device 23a from the displayed list of the patient information, and transmits the selected patient information of the subject to the main receiving device 23a. Here, the control unit 38 controls the communication unit 32 so as to transmit the patient information of the subject to the main receiving device 23a. Thereafter, the control unit 38 erases the registered patient information of the subject in the portable recording medium 6 based on the erasure instruction information acquired from the control unit 28 of the main receiving device 23a. The control unit 38 displays the menu 100 again on the display unit 37 when the erasure of the registered patient information of the subject in the portable recording medium 6 is finished.

Figure 8:
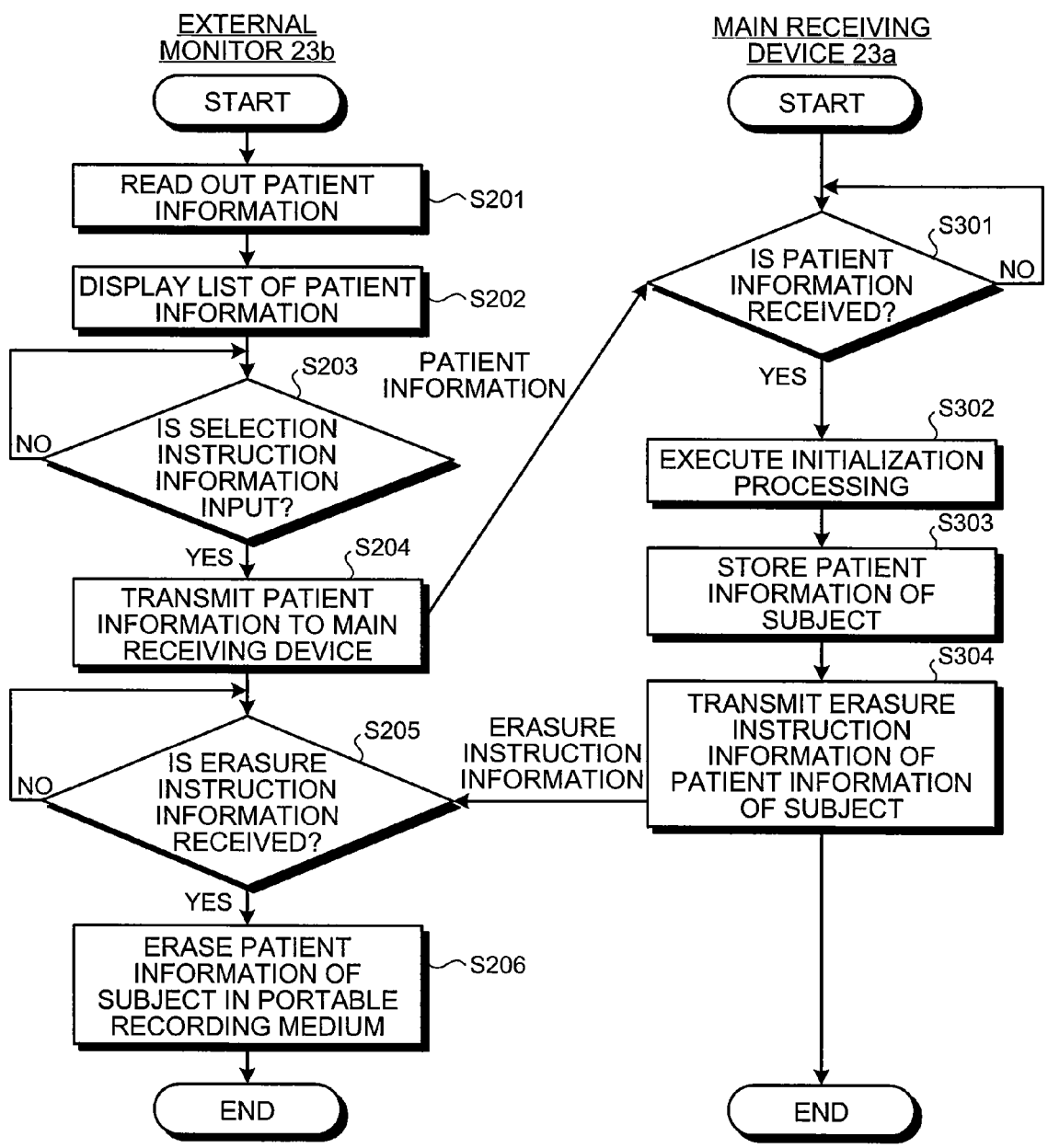
FIG. 8 is a flowchart of each processing procedure of a main receiving device and an external monitor of the receiving apparatus according to the second embodiment.

An operation of the control unit 38 of the external monitor 23b set in the initialization mode and an operation of the control unit 28 performed to initialize the main receiving device 23a based on the patient information of the subject acquired from the external monitor 23b will be described. FIG. 8 is a flowchart of a processing procedure of the control unit 38 of the external monitor 23b set in the initialization mode, and a processing procedure of the control unit 28 performed to initialize the main receiving device 23a based on the patient information of the subject acquired from the external monitor 23b.

In FIG. 8, the external monitor 23b reads out the patient information of one or more test bodies recorded on the portable recording medium 6 which is detachably connected to the external monitor 23b (step S201), and displays a list of the read-out patient information of one or more test bodies (step S202). Here, the control unit 38 is set to the initialization mode by the mode switching unit 38a, and controls the communication unit 33 so as to read out the patient information of one or more test bodies recorded on the portable recording medium 6 connected to the communication unit 33, and acquires the patient information of one or more test bodies from the portable recording medium 6 via the communication unit 33. The control unit 38 displays the list of the patient information of one or more test bodies thus acquired on the display unit 37.

Then, the external monitor 23b monitors whether the selection instruction information giving the selection instruction of desired patient information from the list of the patient information displayed on the display unit 37 is input or not, and continues monitoring of presence/absence of the input of the selection instruction information if the selection instruction information has not been input (No in step S203). Here, the control unit 38 monitors the presence/absence of the selection instruction information supplied from the input unit 36, and continues monitoring of the presence/absence of the input of the selection instruction information until the selection instruction information is supplied from the input unit 36.

On the other hand, the external monitor 23b, when the selection instruction information is input according to the input manipulation on the input unit 36 (Yes in step S203), transmits the patient information of the subject for which the selection instruction is given according to the selection instruction information to the main receiving device 23a (step S204). Here, the control unit 38 receives the selection instruction information from the input unit 36. The information selecting unit 38b selects the patient information of the subject for which the selection instruction is given according to the selection instruction information from the list of the patient information displayed on the display unit 37. The control unit 38 controls the communication unit 32 so as to transmit the patient information of the subject selected by the information selecting unit 38b to the main receiving device 23a. Thus, the patient information of the subject is received by the control unit 28 of the main receiving device 23a via the communication units 12 and 32 and the cable 23d.

Thereafter, the external monitor 23b monitors whether the erasure instruction information giving the erasure instruction of the registered patient information of the subject remaining in the portable recording medium 6 is received from the main receiving device 23a or not, and continues monitoring of the presence/absence of the reception of the erasure instruction information if the erasure instruction information has not been received (No in step S205). Here, the control unit 38 monitors the presence/absence of the erasure instruction information from the control unit 28 of the main receiving device 23a via the communication units 12 and 32 and the cable 23d, and continues monitoring of the presence/absence of the reception of the erasure instruction information until the erasure instruction information from the control unit 28 of the main receiving device 23a is received.

On the other hand, the main receiving device 23a monitors whether the patient information of the subject is received from the external monitor 23b or not and continues monitoring of the presence/absence of the reception of the patient information of the subject if the patient information of the subject has not been received (No in step S301). Here, the control unit 28 monitors the presence/absence of the patient information of the subject received from the control unit 38 of the external monitor 23b via the communication units 12 and 32 and the cable 23d, and continues monitoring of the presence/absence-of the reception of the patient information of the subject until the patient information of the subject is received from the control unit 38 of the external monitor 23b.

Thereafter, the main receiving device 23a, on receiving the patient information of the subject transmitted from the external monitor 23b via the processing of step S204 described above (Yes in step S301), executes the initialization processing based on the patient information of the subject (step S302), and stores the patient information of the subject registered through the initialization processing (step S303). Here, the control unit 28 receives the patient information of the subject from the control unit 38 of the external monitor 23b via the communication units 12 and 32 and the cable 23d. Then, the control unit 28, similarly to steps S104 and S105 mentioned above, registers the patient information of the subject in the main receiving deice 23a and initializes the main receiving device 23a by setting the subject identified by the patient information as the examination target, and stores the patient information registered in the main receiving device 23a in the storage unit 17.

When the initialization is finished as described above, the main receiving device 23a transmits the erasure instruction information to the external monitor 23b to erase the registered patient information of the subject remaining in the portable recording medium 6 (step S304). Here, the control unit 28 recognizes that the initialization of the main receiving device 23a has finished, and controls the communication unit 12 so as to transmit the erasure instruction information to the external monitor 23b. Thus, the erasure instruction information is received by the control unit 38 of the external monitor 23b via the communication units 12 and 32 and the cable 23d.

On the other hand, the external monitor 23b, on receiving the erasure instruction information transmitted from the main receiving device 23a through the processing in step S304 described above (Yes in step S205), erases the registered patient information of the subject in the portable recording medium 6 based on the erasure instruction information (step S206). Here, the control unit 38 receives the erasure instruction information from the control unit 28 of the main receiving device 23a via the communication units 12 and 32 and the cable 23d. The erasure processing unit 38c, based on the erasure instruction information, generates a control signal to erase the registered patient information of the subject remaining in the portable recording medium 6 (i.e., the same information as the patient information registered in the main receiving device 23a), and transmits the control signal to the portable recording medium 6 via the communication unit 33. Thus, the portable recording medium 6 erases the patient information registered in the main receiving device 23a from the stored one or more pieces of patient information. Thus, the control unit 28 of the main receiving device 23a controls the erasure processing of erasing the registered patient information in the portable recording medium 6 using the erasure instruction to the control unit 38 of the external monitor 23b.

Figure 9:
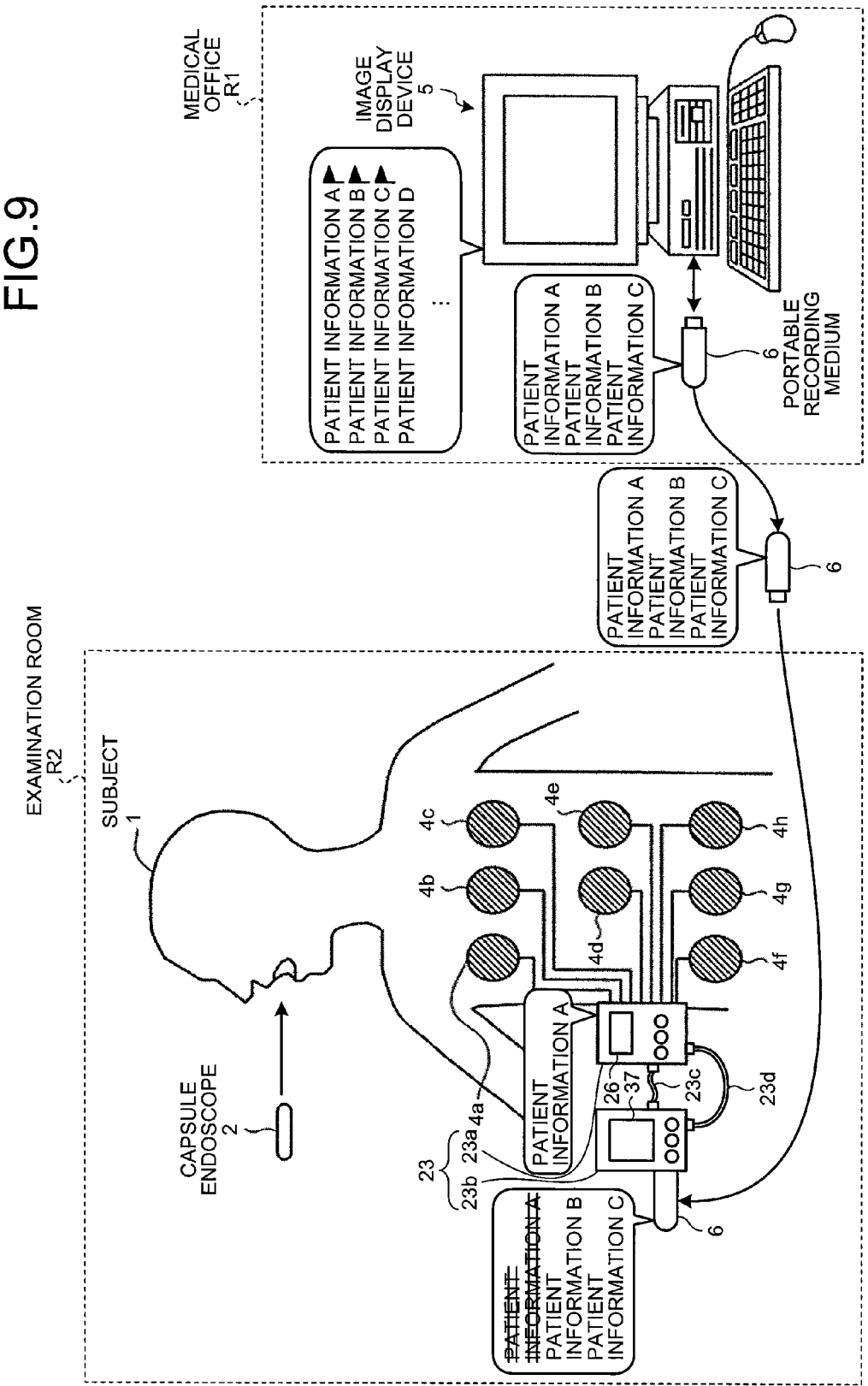
FIG. 9 is a schematic diagram illustrating how patient information of a subject as an examination target among patient information of plural test bodies recorded on the portable recording medium is registered in the main receiving device.
Figure 10:
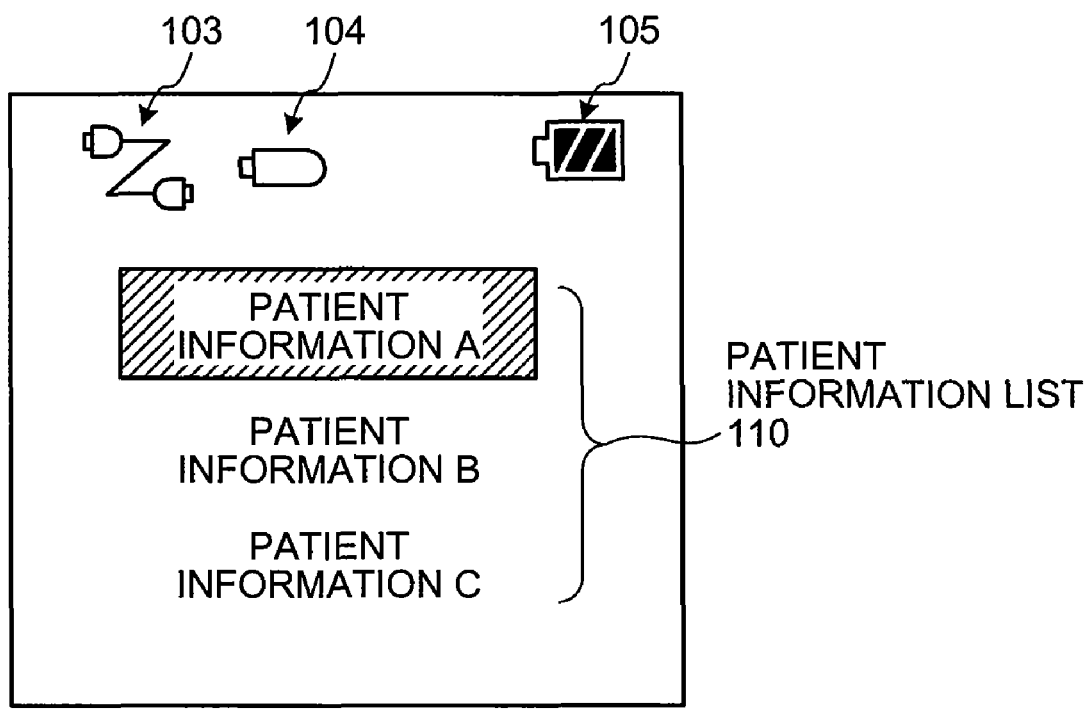
FIG. 10 is a schematic diagram illustrating a state where a list of patient information is displayed on a display unit of the external monitor.

Effects of the respective elements in the in-vivo information acquiring system according to the second embodiment will be specifically described based on an example in which the receiving apparatus 23 is attached to the subject 1 as the examination target to which the capsule endoscope 2 is introduced. FIG. 9 is a schematic diagram illustrating how the patient information of the subject 1 as the examination target among the patient information of plural test bodies recorded on the portable recording medium 6 is registered in the main receiving device 23a for the initialization of the main receiving device 23a. FIG. 10 is a schematic diagram illustrating how the list of the patient information is displayed on the display unit 37 of the external monitor 23b. Hereinbelow, the effects of the respective elements in the in-vivo information acquiring system according to the second embodiment will be described with reference to FIGS. 9 and 10.

The portable recording medium 6 is detachably connected to the image display device 5 installed in, for example, the medical office R1, and the patient information of the plural test bodies including the patient information A of the subject 1 as the examination target is recorded on the portable recording medium 6 in an erasable manner. For example, pieces of patient information A, B, and C of the plural test bodies from the patient information of the plural test bodies (patient information A, B, C, D, . . . ) managed by the image display device 5 is recorded on the portable recording medium 6 in an integrated manner. When the plural pieces of patient information A, B, and C are written into the portable recording medium 6, for example, the image display device 5 affixes flags indicating that the plural pieces of patient information A, B, and C are taken out by the portable recording medium 6 to the patient information A, B, and C (i.e., original patient information A, B, and C under the integrated management).

On the other hand, the portable recording medium 6 in which the plural pieces of patient information A, B, and C of the plural test bodies are recorded in an erasable manner is carried to the examination room R2 where the subject 1 waits. The receiving apparatus 23 which accumulates the image data acquired through image capturing by the capsule endoscope 2 is attached to the subject 1 waiting in the examination room R2. The receiving antennas 4a to 4h are arranged on the body surface of the subject 1 in a dispersed manner, and the main receiving device 23a to which the receiving antennas 4a to 4h are connected is attached to the torso of the subject 1, for example. Further, the external monitor 23b is detachably connected to the main receiving device 23a via the cables 23c and 23d. The receiving apparatus 23 is uniquely determined as the one which serves for accumulating the image data of the subject 1, when the receiving apparatus 23 is attached to the subject 1.

Similarly to the receiving apparatus 3 of the first embodiment described above, predetermined operation check is performed on the main receiving device 23a of the receiving apparatus 23 attached to the subject 1 in advance. Further, the external monitor 23b connected to the main receiving device 23a is checked in advance and it is confirmed that the external monitor 23b can operate normally.

The portable recording medium 6 in which the plural pieces of patient information A, B, and C of the plural test bodies are recorded in an erasable manner is detachably connected to the receiving apparatus 23 which is attached to the subject 1. Specifically, when the receiving apparatus 23 is attached to the subject 1 or after the receiving apparatus 23 is attached to the subject 1, the portable recording medium 6 is detachably connected to the external monitor 23b of the receiving apparatus 23. Here, the control unit 38 of the external monitor 23b follows processing procedure of steps S201 to S206 mentioned above, and the control unit 28 of the main receiving device 23a follows the processing procedure of steps S301 to 304 mentioned above.

Specifically, the external monitor 23b is set to the initialization mode, reads out the patient information A, B, and C of the plural test bodies recorded on the portable recording medium 6, and displays the list of the plural pieces of patient information A, B, and C of the plural test bodies on the display unit 37. Here, the display unit 37 displays a patient information list 110 which indicates the plural pieces of patient information read out from the portable recording medium 6 as shown in FIG. 10. The examiner can easily confirm whether the patient information A of the subject 1 to whom the main receiving device 23a is attached is included or not by visually confirming the patient information list 110. The display unit 37 further displays the connection marks 103 and 104, and the remaining power amount mark 105 mentioned above together with the patient information list 110.

When the patient information list 110 includes the patient information A of the subject 1, the examiner performs an input manipulation of the selection instruction information to give the selection instruction of the patient information A of the subject 1 from the patient information list 110 as shown in FIG. 10. The input unit 36 of the external monitor 23b inputs the selection instruction information giving the selection instruction of the patient information A to the control unit 38. The control unit 38 selects the patient information A from the patient information list 110 based on the selection instruction information supplied from the input unit 36, and makes the control unit 28 of the main receiving device 23a acquire the selected patient information A.

The control unit 28 of the main receiving device 23a that receives the patient information A transmitted by the external monitor 23b updates the patient information of the subject 1 as the examination target with the acquired patient information A and registers the patient information A in the main receiving device 23a. Here, the control unit 28 stores the patient information A in the storage unit 17, and displays the registered patient information A on the display unit 26. The examiner can easily confirm whether the patient information registered in the main receiving device 23a matches with the subject to whom the main receiving device 23a is attached, by visually confirming the patient information A displayed on the display unit 26 of the main receiving device 23a.

Further, the control unit 28 of the main receiving device 23a controls the erasure processing of the registered patient information A remaining in the portable recording medium 6 connected to the external monitor 23b. The control unit 28 transmits the erasure instruction information giving the erasure instruction of the registered patient information A in the portable recording medium 6 to the control unit 38 of the external monitor 23b. The control unit 38 of the external monitor 23b erases the registered patient information A in the portable recording medium 6 based on the received erasure instruction information from the control unit 28. The portable recording medium 6 erases the registered patient information A among the plural pieces of patient information A, B, and C of the plural test bodies.

Thereafter, the portable recording medium 6 which stores the remaining patient information B and C in an erasable manner is removed from the external monitor 23b, and sequentially connected to each of receiving apparatuses of test bodies identified by the patient information B and C. The portable recording medium 6 sequentially supplies the patient information matching with the subject to each receiving apparatus. Thus, since plural pieces of patient information to be sequentially supplied to the plural receiving apparatuses is recorded on the portable recording medium 6 in an erasable manner, the number the patient information is taken out from the image display device 5 in the medical office R1, for example, can be reduced, and the operation of supplying the patient information to the receiving apparatus attached to the subject can be made less cumbersome.

On the other hand, the main receiving device 23a initialized based on the patient information A accumulates the image data received from the capsule endoscope 2 as the image data of the subject 1. Further, the main receiving device 23a is attached to the subject 1 identified by the patient information A and is uniquely determined with respect to the subject 1, as described above. Therefore, when the capsule endoscope 2 is introduced into the subject 1, the main receiving device 23a does not mistake the subject 1 as the examination target for another subject, and can correctly accumulate the image data acquired through image capturing by the capsule endoscope 2 as the image data of the subject 1.

Thereafter, the image data of the subject 1 accumulated in the main receiving device 23a is taken into the image display device 5 in the medical office R1 with the main receiving device 23a or the portable recording medium 6 as a media. Here, the image display device 5, similarly to the first embodiment, recognizes that the patient information A taken out by the portable recording medium 6 is returned together with the image data, and deletes the flag affixed to the original patient information A under the integrated management. The same applies to the patient information B and C taken out by the portable recording medium 6.

As described above, in the second embodiment of the invention, the portable recording medium in which the patient information of one or more test bodies is recorded in an erasable manner is employed as a media, and the patient information of one or more test bodies recorded on the portable recording medium is acquired and displayed as a list. Patient information of a desirable subject is selected from the displayed list of patient information of one or more test bodies, and the selected patient information of the subject is registered in the main receiving device. Further, the patient information which is registered in the main receiving device is erased from the patient information of one or more test bodies remaining in the portable recording medium. Therefore, in addition to the effects and advantages of the first embodiment described above, the operation of registering the patient information in the main receiving device can be made less cumbersome, as the patient information of the plural test bodies is recorded in an erasable manner in the portable recording medium.

A third embodiment of the invention will be described. In the second embodiment described above, the portable recording medium 6 in which the patient information of the subject is recorded in an erasable manner is detachably connected to the external monitor 23b, and the patient information in the portable recording medium 6 is acquired by the main receiving device 23a via the external monitor 23b. In the third embodiment, a recording medium in which the patient information of the subject is recorded in an erasable manner is arranged in the external monitor, and the patient information of the subject is supplied to the main receiving device with the use of the recording medium of the external monitor as a media.

Figure 11:
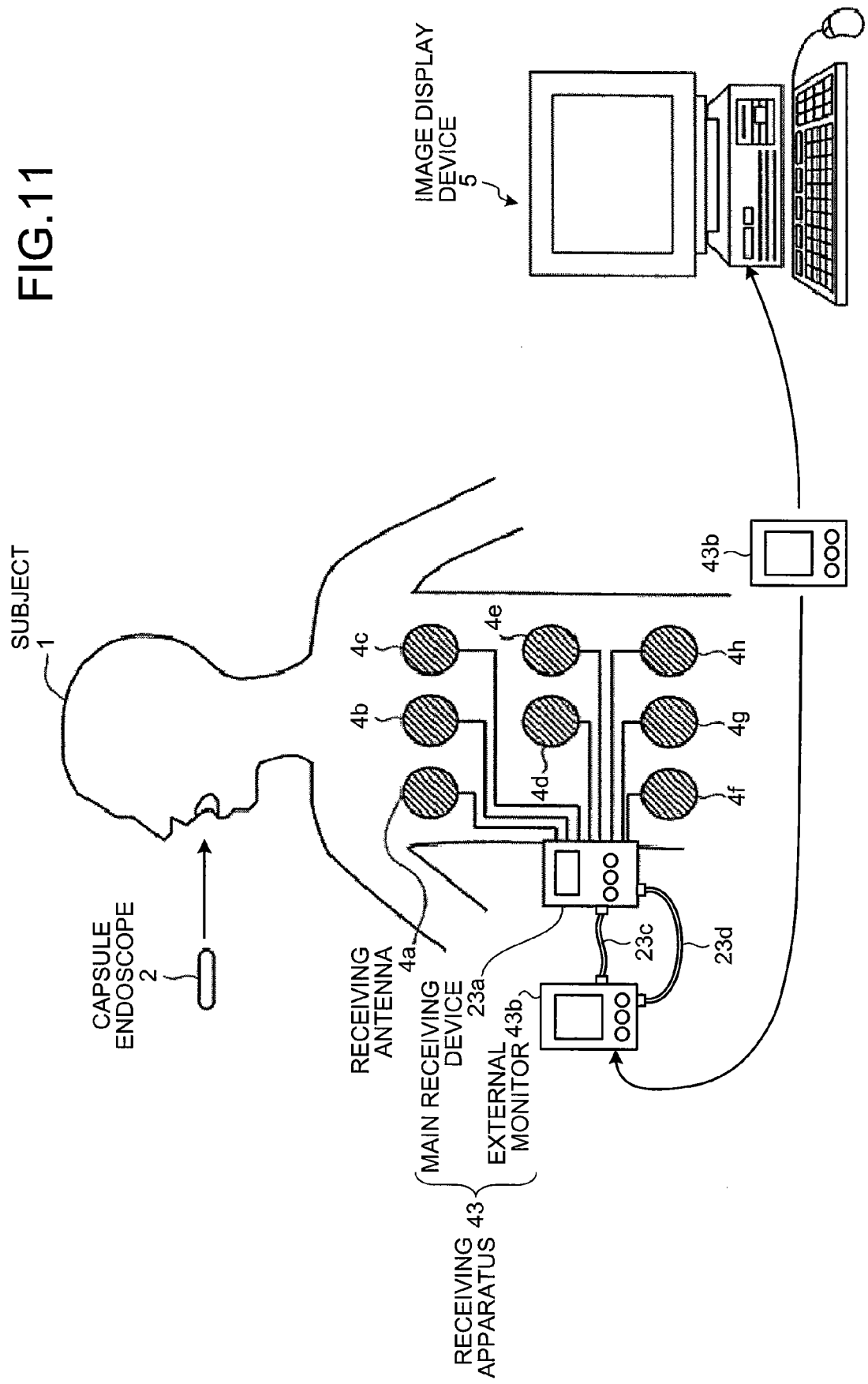
FIG. 11 is a schematic diagram of one exemplary structure of an in-vivo information acquiring system according to a third embodiment of the invention.

FIG. 11 is a schematic diagram of one exemplary structure of an in-vivo information acquiring system according to the third embodiment of the invention. As shown in FIG. 11, the in-vivo information acquiring system according to the third embodiment includes a receiving apparatus 43 in place of the receiving apparatus 23 of the in-vivo information acquiring system according to the second embodiment described above, and the main receiving device 23a acquires the patient information of the subject with the use of an external monitor 43b of the receiving apparatus 43 as a media in place of the portable recording medium 6. In other respects, the structure of the third embodiment is the same as the structure of the second embodiment, and the same elements are denoted by the same reference characters.

The receiving apparatus 43 includes a main receiving device 23a to which the receiving antennas 4a to 4h are connected, and the external monitor 43b detachably connected to the main receiving device 23a. The external monitor 43b, similarly to the external monitor 23b of the receiving apparatus 23 according to the second embodiment, is detachably connected to the main receiving device 23a via the cables 23c and 23d. Further, the external monitor 43b has an information recording function to record the patient information of one or more test bodies in an erasable manner and a display function to display the stored patient information of one or more test bodies. In other words, the external monitor 43b functions as an external display unit which displays the patient information of the subject to be registered in the main receiving device 23a and as a portable recording medium in which the patient information of the subject is recorded in an erasable manner.

Figure 12:
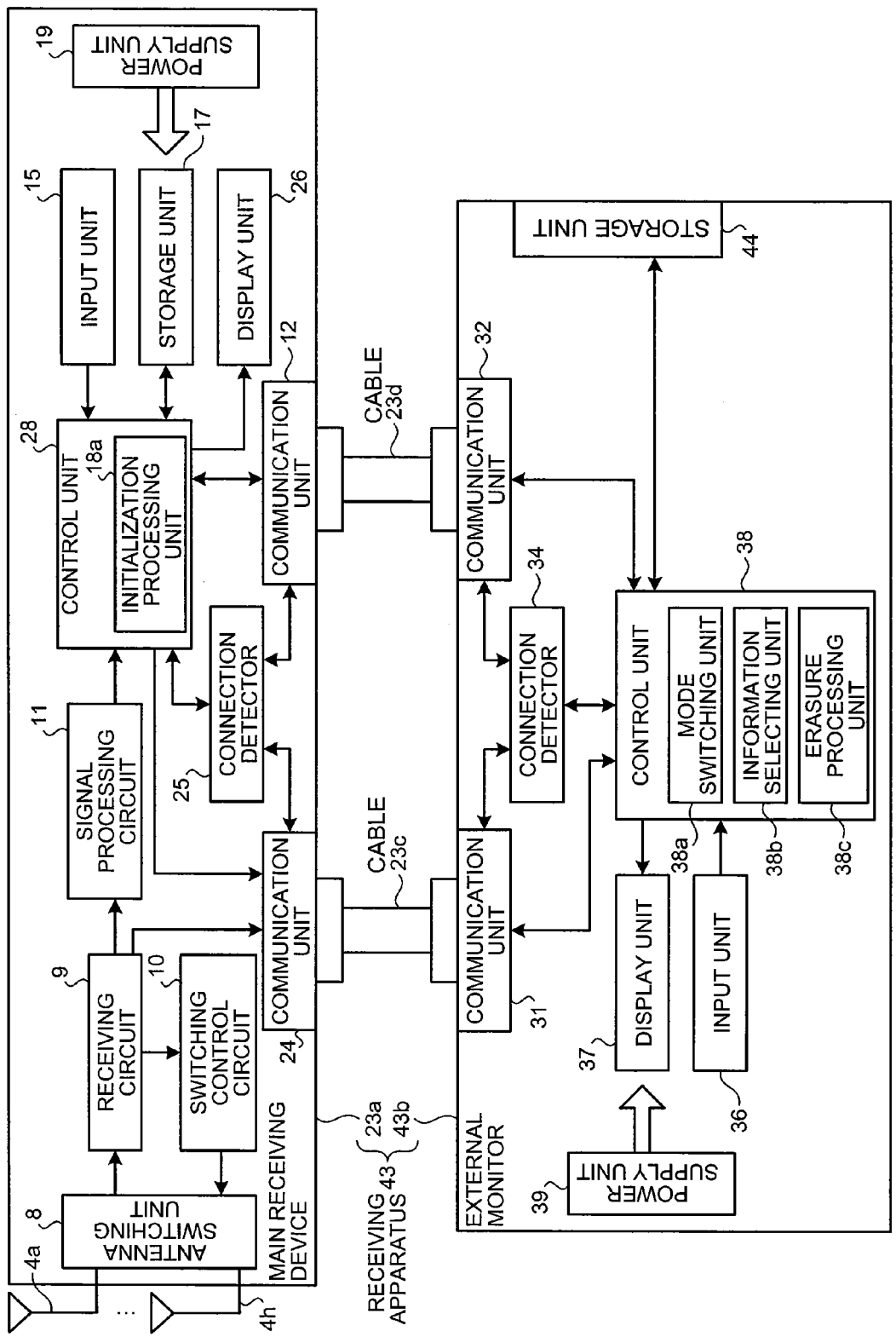
FIG. 12 is a schematic block diagram of one exemplary structure of a receiving apparatus according to the third embodiment.

A structure of the receiving apparatus 43 according to the third embodiment of the invention will be described. FIG. 12 is a schematic block diagram of one exemplary structure of the receiving apparatus 43 according to the third embodiment. As shown in FIG. 12, the receiving apparatus 43 includes a storage unit 44 in place of the communication unit 33 of the external monitor 23b of the receiving apparatus 23 according to the second embodiment. In other respects, the structure of the receiving apparatus 43 is the same as that of the receiving apparatus 23 according to the second embodiment, and the same elements are denoted by the same reference characters.

The storage unit 44 is realized with a storage, such as an HDD and a flash memory, which stores information in an erasable manner, and stores information for which a recording instruction is given by the control unit 38 in an erasable manner. Specifically, the control unit 38, when the image display device 5 and the communication unit 32 are connected via a predetermined cable, acquires the patient information of one or more test bodies under the integrated management of the image display device 5. The control unit 38, then, stores the patient information of one or more test bodies acquired from the image display device 5 into the storage unit 44. The storage unit 44 stores the patient information of one or more test bodies for which the control unit 38 gives the recording instruction in an erasable manner. Since the external monitor 43b is portable, the storage unit 44 functions as a portable recording medium which performs delivery of the patient information of the subject between the image display device 5 and the main receiving device 23a.

The control unit 38 of the external monitor 43b, on receiving the connection detection result indicating that the communication unit 12 and the communication unit 32 are connected via the cable 23d from the connection detector 34, displays the connection mark indicating that the communication unit 12 and the communication unit 32 are in a connected state on the display unit 37, and displays the option 102 for the initialization mode mentioned above on the display unit 37. Further, the control unit 38 displays a list of patient information of one or more test bodies read out from the storage unit 44 on the display unit 37, and similarly to the second embodiment, selects the patient information of the subject to be acquired by the main receiving device 23a. Further, the control unit 38 erases the registered patient information of the subject remaining in the storage unit 44 based on the erasure instruction information received from the control unit 28 of the main receiving device 23a.

As described above, the third embodiment of the invention is configured so as to have substantially the same functions as those of the second embodiment, the recording medium in which the patient information of the subject is recorded in an erasable manner is arranged in the portable external monitor, and the patient information of the subject is supplied to the main receiving device via the recording medium of the external monitor as a media. Therefore, in addition to the enjoyment of the same effects and the advantages as those of the second embodiment, the patient information of the subject recorded on the recording medium in an erasable manner can be easily confirmed before the patient information of the subject is supplied to the main receiving device.

A fourth embodiment of the invention will be described. In the second embodiment described above, the patient information of a desirable subject is selected from the list of patient information of the test bodies displayed by the display unit 37 based on the selection instruction information supplied from the input unit 36. In the fourth embodiment, patient information is read out from an ID tag (RF-ID tag, optically readable code, or the like) attached to the subject, and the patient information matching with the read-out patient information is selected from the patient information of the test bodies displayed in the list on the display unit 37.

Figure 13:
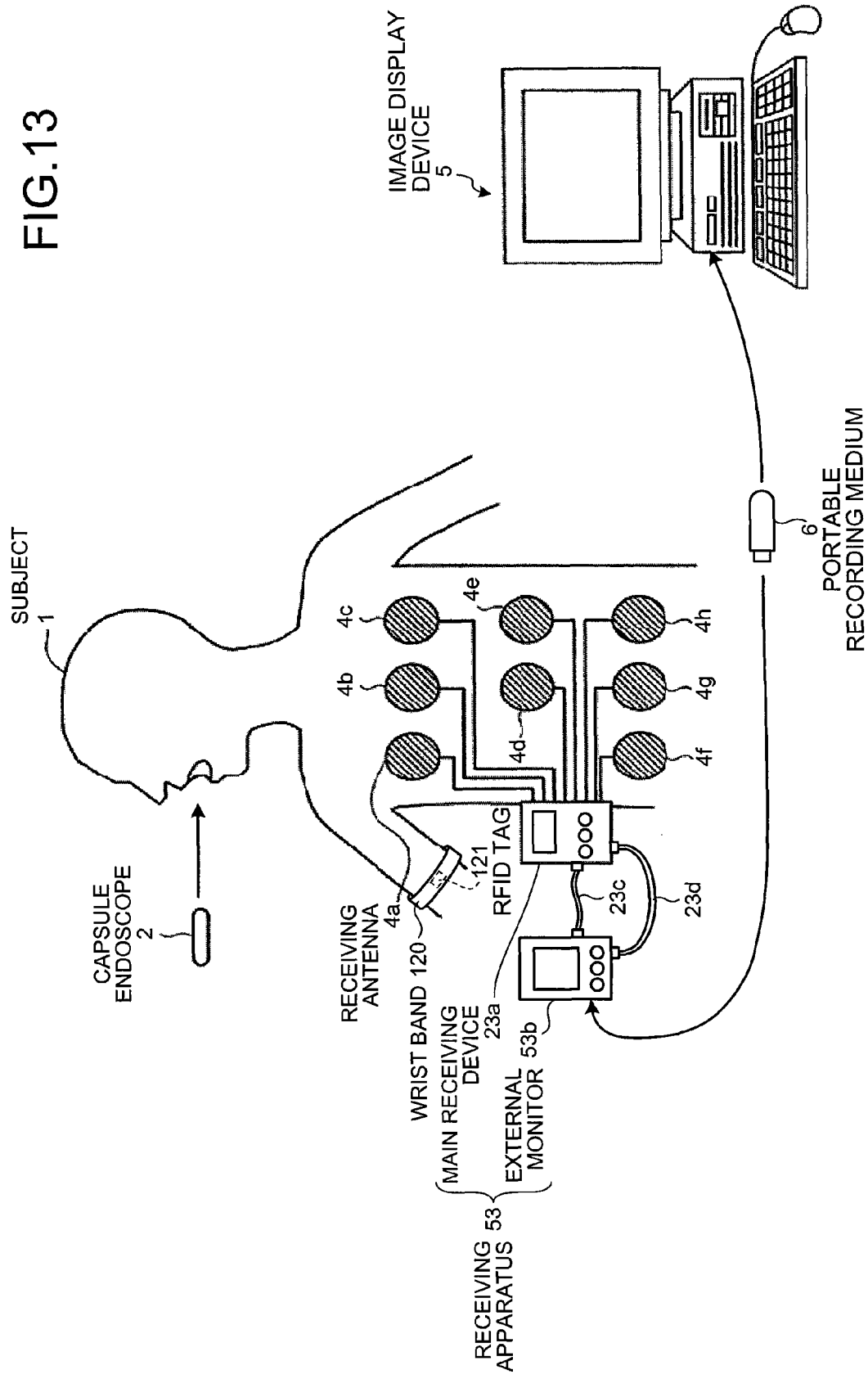
FIG. 13 is a schematic diagram of one exemplary structure of an in-vivo information acquiring system according to a fourth embodiment of the invention.

FIG. 13 is a schematic diagram of one exemplary structure of an in-vivo information acquiring system according to the fourth embodiment of the invention. As shown in FIG. 13, the in-vivo information acquiring system according to the fourth embodiment includes a receiving apparatus 53 in place of the receiving apparatus 23 of the in-vivo information acquiring system according to the second embodiment. Further, a wrist band 120, to which an ID tag (RF-ID tag 121) recording the patient information A of the subject is attached, is attached to the subject 1 as the examination target. In other respects, the structure of the fourth embodiment is the same as the structure of the second embodiment, and the same elements are denoted by the same reference characters.

The receiving apparatus 53 includes the main receiving device 23*a* to which the receiving antennas 4*a* to 4*h* are connected, and an external monitor 53*b* which is detachably connected to the main receiving device 23*a*. The external monitor 53*b*, similarly to the external monitor 23*b* of the receiving apparatus 23 according to the second embodiment, is detachably connected to the main receiving device 23*a* via the cables 23*c* and 23*d*, and detachably connected to the portable recording medium 6 via the connector 6*a* and the like. Further, the external monitor 53*b* has an ID reading function to read out the patient information (i.e., the patient information of the subject 1) recorded in the RFID tag 121 of the wrist band 120 attached to the subject 1, for example. ID reading function can be an RF-ID reader or optical code reader or the like, which matches with the type of ID.

Figure 14:
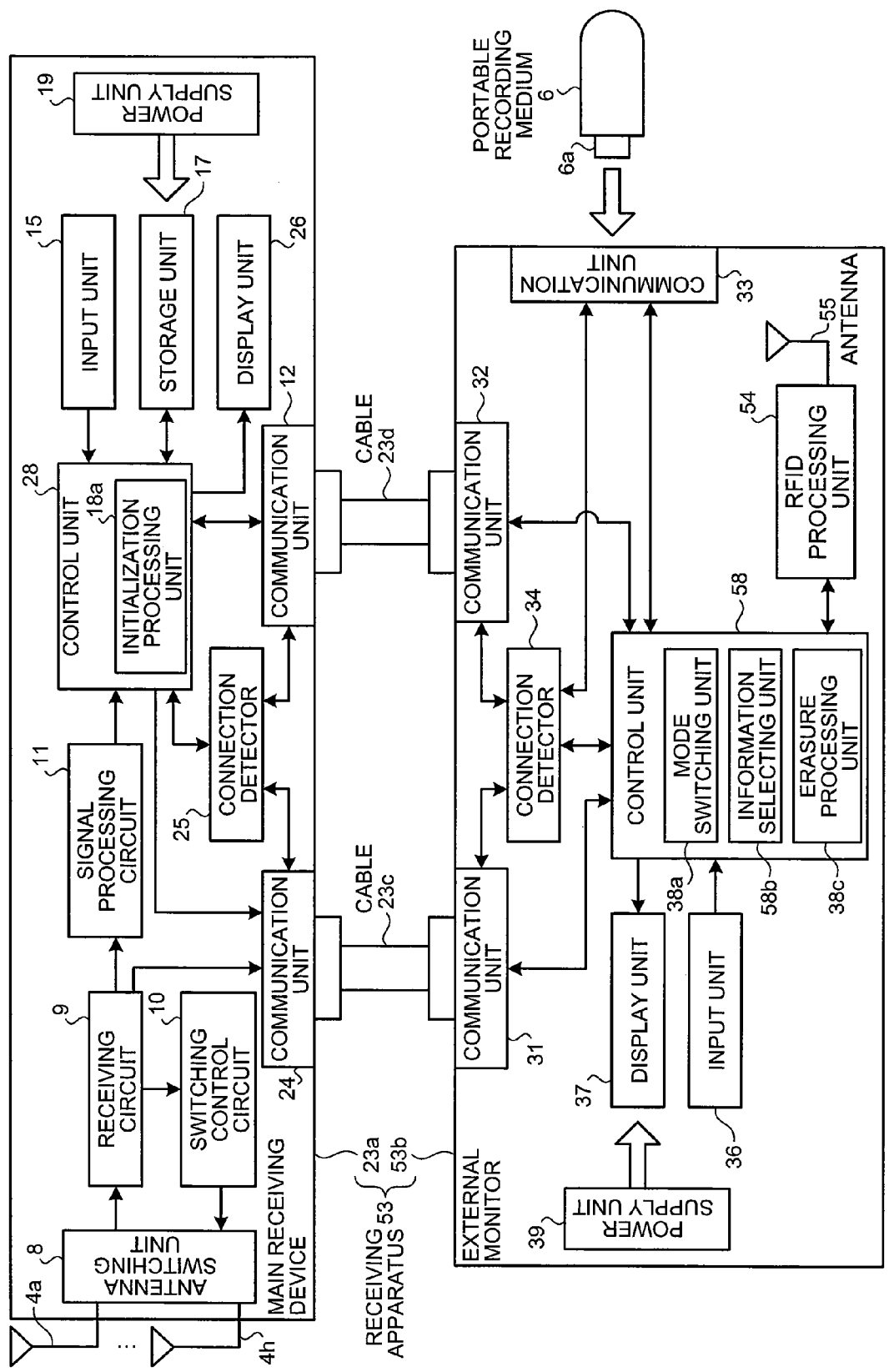
FIG. 14 is a schematic block diagram of an exemplary structure of a receiving apparatus according to the fourth embodiment.

A structure of the receiving apparatus 53 according to the fourth embodiment of the invention will be described. FIG. 14 is a schematic block diagram of one exemplary structure of the receiving apparatus 53 according to the fourth embodiment. As shown in FIG. 14, the receiving apparatus 53 includes a control unit 58 in place of the control unit 38 of the external monitor 23*b* of the receiving apparatus 23 according to the second embodiment, and further includes an RFID processing unit 54 and an antenna 55. In other respects, the structure of the fourth embodiment is the same as the structure of the second embodiment, and the same elements are denoted by the same reference characters.

The RFID processing unit 54 functions as an RFID reader which reads out the patient information recorded in the RFID tag 121 of the wrist band 120 attached to the subject 1, for example. Specifically, the RFID processing unit 54 is connected to the antenna 55 and causes transmission/reception of electric waves between the antenna 55 and the RFID tag 121 by supplying the power to the antenna 55. The RFID processing unit 54 reads out the patient information of the subject 1 from the RFID tag 121 via the electric waves. The RFID processing unit 54 transmits the patient information of the subject 1 read out from the RFID tag 121 to the control unit 58.

The control unit 58 has substantially the same function as the control unit 38 of the external monitor 23*b* according to the second embodiment, and further controls driving of the RFID processing unit 54 based on instruction information supplied from the input unit 36. Further, the control unit 58 selects the patient information to be acquired by the main receiving device 23*a* based on the patient information received from the RFID processing unit 54. The control unit 58 has the mode switching unit 38*a* and the erasure processing unit 38*c* mentioned above, and an information selecting unit 58*b* in place of the information selecting unit 38*b* mentioned above.

The information selecting unit 58*b* selects the patient information to be acquired by the main receiving device 23*a* from the patient information of one or more test bodies displayed as a list on the display unit 37 based on the patient information read out by the RFID processing unit 54. The information selecting unit 58*b* selects the patient information matching with the patient information read out by the RFID processing unit 54 from the patient information of one or more test bodies displayed as the list on the display unit 37. The control unit 58 makes the main receiving device 23*a* acquire the patient information of the subject selected by the information selecting unit 58*b*.

Figure 15:
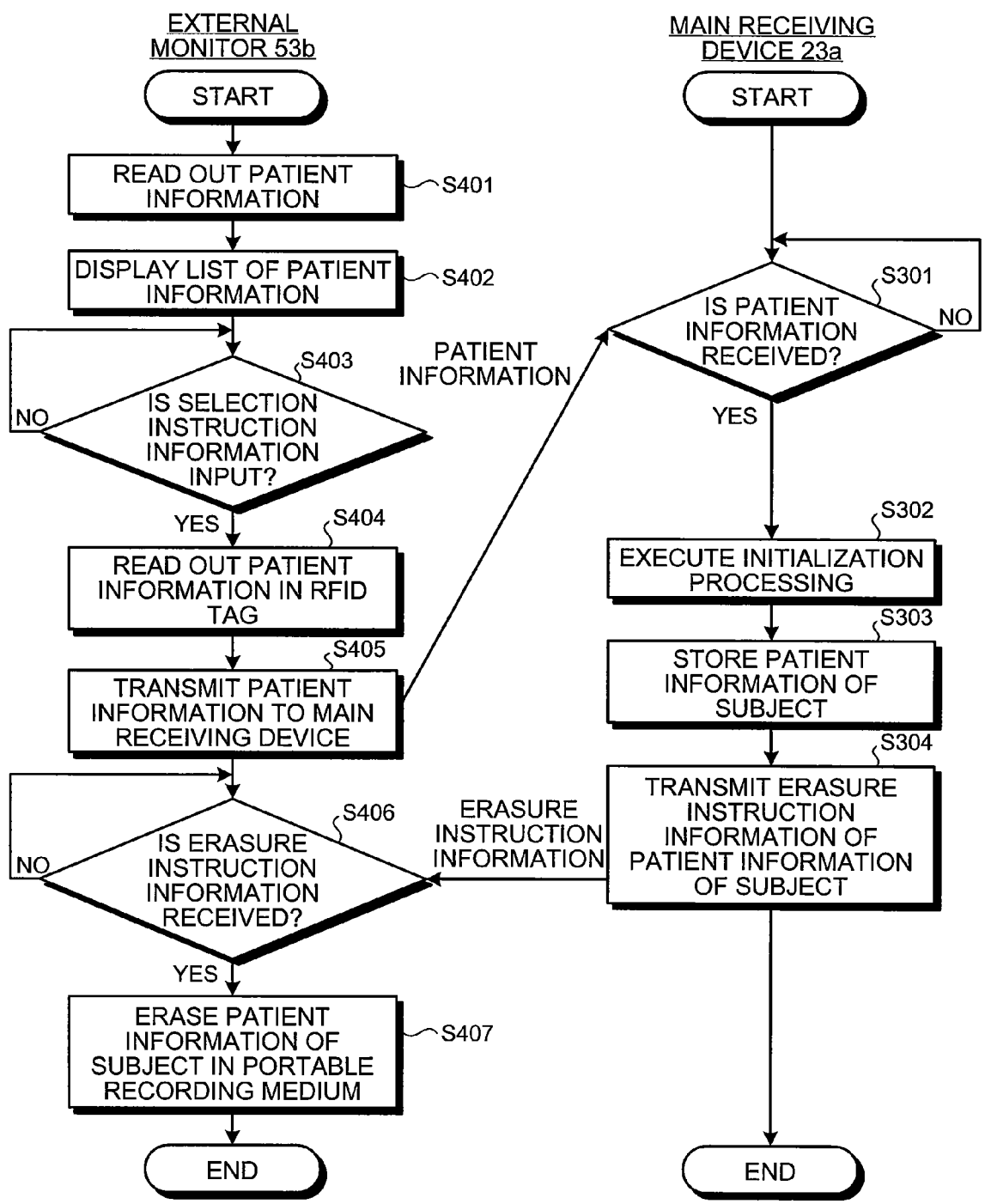
FIG. 15 is a flowchart of each processing procedure of a main receiving device and an external monitor of the receiving apparatus according to the fourth embodiment.
Figure 16:
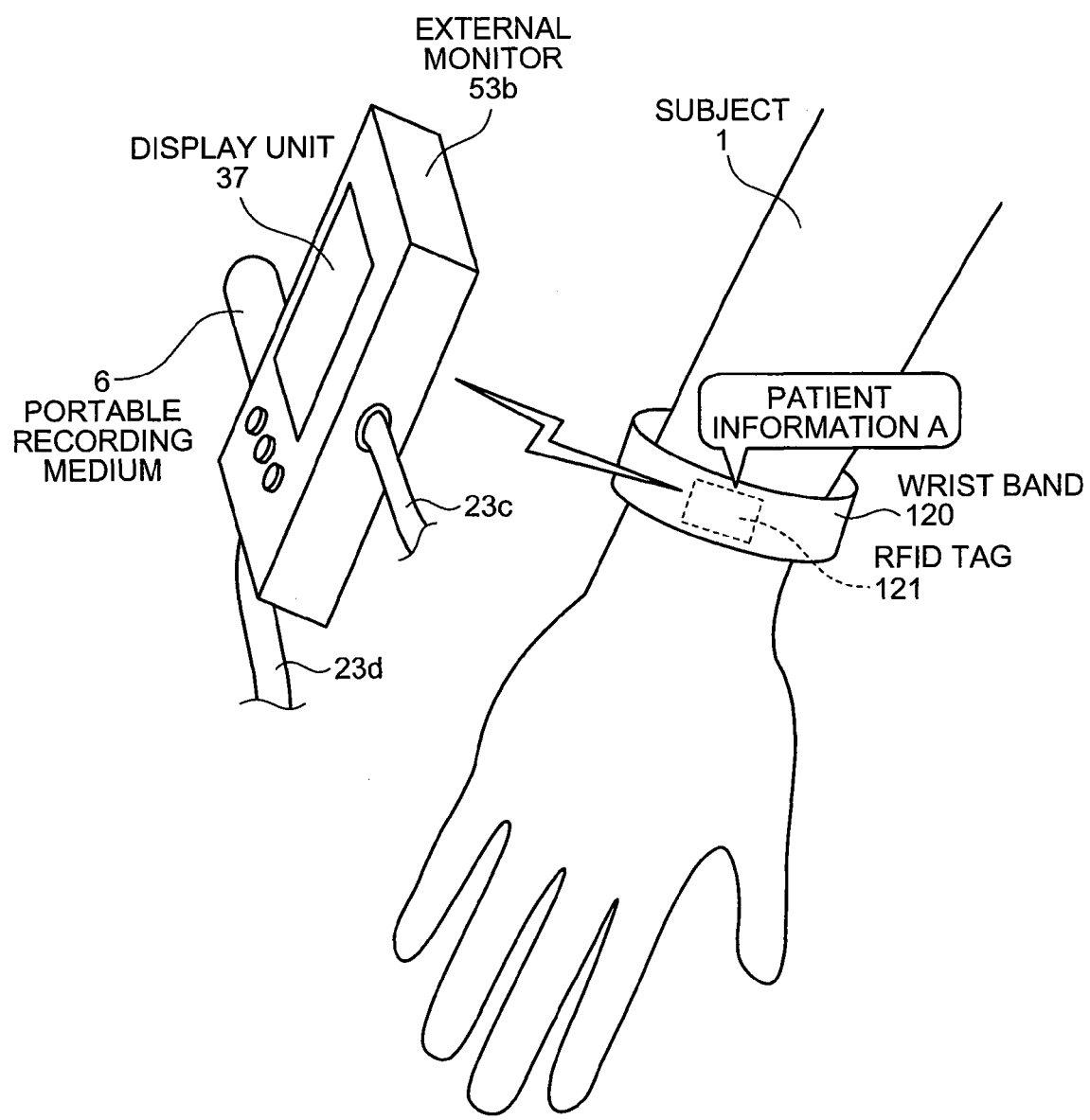
FIG. 16 is a schematic view showing how patient information recorded in an RFID tag of a wrist band is read out.

An operation of the control unit 58 of the external monitor 53*b* set to the initialization mode and an operation of the control unit 28 which initializes the main receiving device 23*a* based on the patient information of the subject acquired from the external monitor 53*b* will be described. FIG. 15 is a flowchart of a processing procedure of the control unit 58 of the external monitor 53*b* set to the initialization mode and a processing procedure of the control unit 28 which initializes the main receiving device 23*a* based on the patient information of the subject acquired from the external monitor 53*b*. FIG. 16 is a schematic view showing how the external monitor 53*b* reads out the patient information recorded in the RFID tag 121 of the wrist band 120.

In FIG. 15, the external monitor 53*b* reads out the patient information of one or more test bodies recorded on the portable recording medium 6, similarly to steps S201 and S202 mentioned above, and displays a list of read-out patient information of one or more test bodies on the display unit 37 (steps S401, S402). Then, the external monitor 53*b* monitors whether instruction information (hereinafter referred to as reading instruction information) instructing reading of the patient information from the RFID tag 121 of the wrist band 121 attached to the subject 1 is input or not, and continues monitoring of the presence/absence of the input of the reading instruction information, if the reading instruction information has not been input (No in step S403). Here, the control unit 58 monitors the presence/absence of the input of the reading instruction information supplied from the input unit 36, and continues monitoring of the presence/absence of the input of the reading instruction information until the reading instruction information is supplied from the input unit 36.

On the other hand, when the reading instruction information is input through the input manipulation on the input unit 36 (Yes in step S403), the external monitor 53*b* reads out the patient information recorded in the RFID tag 121 based on the reading instruction information (step S404). Specifically, the external monitor 53*b* is held near the wrist band 120 attached to the subject 1 as shown in FIG. 16, and reads out the patient information A of the subject 1 recorded in the RFID tag 121 of the wrist band 120. The control unit 58 receives the reading instruction information from the input unit 36, controls the driving of the RFID processing unit 54 based on the reading instruction information, and makes the RFID processing unit 54 read out the patient information A recorded in the RFID tag 121. The control unit 58 acquires the patient information A read out by the RFID processing unit 54.

The external monitor 53*b* selects the patient information to be acquired by the main receiving device 23*a* from the patient information of one or more test bodies displayed as the list on the display unit 37 based on the patient information read out from the RFID tag 121, and transmits the selected patient information to the main receiving device 23*a* (step S405).

Here, the information selecting unit 58b selects the patient information A which matches with the patient information read out by the RFID processing unit 54 from the patient information (for example, the patient information A, B, and C) of one or more test bodies displayed as the list on the display unit 37. The control unit 58 controls the communication unit 32 so as to transmit the patient information A of the subject 1 selected by the information selecting unit 58b to the main receiving device 23a. Thus, the patient information A of the subject 1 is received by the control unit 28 of the main receiving device 23a via the communication units 12, 32 and the cable 23d.

Thereafter, the external monitor 53b, similarly to steps S205 and S206 mentioned above, monitors whether the erasure instruction information is received from the main receiving device 23a or not, and the external monitor 53, on receiving the erasure instruction information from the main receiving device 23a, erases the registered patient information of the subject in the portable recording medium 6 based on the erasure instruction information (steps S406, S407).

In the fourth embodiment of the invention, the RFID tag recording the patient information of the subject is attached to the wrist band, though the invention is not limited thereto; and the RFID tag in which the patient information of the subject is recorded may be attached to a card or a portable commodity such as a case carried by the subject, or may be attached to clothes such as a garment or a belt attached to the subject. In brief, the RFID tag may be attached to anything as far as the RFID tag is uniquely determined with respect to the subject.

Further, in the fourth embodiment of the invention, the RFID processing unit and the antenna are arranged in the external monitor detachably connected to the main receiving device, though the invention is not limited thereto; and the RFID processing unit which reads out the patient information of the subject recorded in the RFID tag and the antenna may be arranged in the main receiving device. Specifically, the RFID processing unit and the antenna may be arranged in the main receiving device 3a of the receiving apparatus 3 according to the first embodiment, and the structure may be formed so that the patient information to be registered in the main receiving device 3a is selected based on the patient information read out by the RFID processing unit.

As described above, the fourth embodiment of the invention has substantially the same functions as those of the second embodiment, the patient information recorded in the RFID tag uniquely determined with respect to the subject is read out, the patient information of the subject matching with the read-out patient information is selected from the displayed list of the patient information of one or more test bodies, and the selected patient information of the subject is registered in the main receiving device. Therefore, in addition to the enjoyment of the same effects and advantages of the second embodiment, the patient information of the subject to be registered in the main receiving device can be easily selected from the displayed list of the patient information of one or more test bodies.

A fifth embodiment of the invention will be described. In the second embodiment described above, the transmission and reception of the patient information is performed between the main receiving device 23a and the external monitor 23b via the cable 23d, however, in the fifth embodiment, the patient information is transmitted/received by infrared communication between the main receiving device and the external monitor.

FIG. 17 is a schematic diagram of one exemplary structure of an in-vivo information acquiring system according to the fifth embodiment of the invention. As shown in FIG. 17, the in-vivo information acquiring system according to the fifth embodiment includes a receiving apparatus 63 in place of the receiving apparatus 23 of the in-vivo information acquiring system according to the second embodiment. In other respects, the structure of the fifth embodiment is the same as the structure of the second embodiment, and the same elements are denoted by the same reference characters.

The receiving apparatus 63 includes a main receiving device 63a to which the receiving antennas 4a to 4h are connected, and an external monitor 63b which is detachably connected to the main receiving device 63a. The main receiving device 63a, similarly to the main receiving device 23a of the receiving apparatus 23 according to the second embodiment, is attached to the subject 1 as the examination target, receives the radio signals from the capsule endoscope 2 via one of the receiving antennas 4a to 4h, and sequentially accumulates the image data included in the received radio signals, in other words, the image data acquired through image capturing by the capsule endoscope 2. Further, the main receiving device 63a is detachably connected to the external monitor 63c via the cable 23c and transmits the image signals to the external monitor 63c via the cable 23c.

The external monitor 63b, similarly to the external monitor 23b of the receiving apparatus 23 according to the second embodiment, receives the image signals from the main receiving device 63a via the cable 23c, generates the image data based on the received image signals, and displays the image (in other words, the image acquired through image capturing by the capsule endoscope 2) based on the obtained image data on a monitor. Further, the external monitor 63b is detachably connected to the portable recording medium 6, reads out the patient information of one or more test bodies recorded on the portable recording medium 6, and displays a list of the read-out patient information of one or more test bodies.

The main receiving device 63a and the external monitor 63b as described above have an infrared communication function to transmit/receive the patient information of the subject or the erasure instruction information. The external monitor 63b transmits the patient information for which the selection instruction is given among the patient information of one or more test bodies displayed as the list to the main receiving device 63a by infrared communication. The main receiving device 63a receives the patient information of the subject by infrared communication, and initializes based on the received patient information of the subject similarly to the main receiving device 23a of the receiving apparatus 23 according to the second embodiment. Further, the main receiving device 63a transmits the erasure instruction information to the external monitor 63b by infrared communication. The external monitor 63b receives the erasure instruction information by infrared communication, and erases the registered patient information in the portable recording medium 6 based on the erasure instruction information, similarly to the external monitor 23b of the receiving apparatus 23 according to the second embodiment.

A structure of the receiving apparatus 63 according to the fifth embodiment of the invention will be described. FIG. 18 is a schematic block diagram of one exemplary structure of the receiving apparatus 63 according to the fifth embodiment. As shown in FIG. 18, the receiving apparatus 63 includes the main receiving device 63a and the external monitor 63b. The main receiving device 63a includes an infrared communication unit 64 in place of the communication unit 12 of the main receiving device 23a according to the second embodiment, and a control unit 66 in place of the control unit 28. On the other hand, the external monitor 63b includes an infrared communication unit 65 in place of the communication unit 32 of the external monitor 23b of the second embodiment, and a control unit 67 in place of the control unit 38. In other respects, the structure of the fifth embodiment is the same as the structure of the second embodiment, and the same elements are denoted by the same reference characters.

The infrared communication units 64 and 65 function as infrared communication units that perform infrared communication between the main receiving device 63a and the external monitor 63b. Specifically, the infrared communication unit 65 transmits the patient information of the subject for which a transmission instruction is given by the control unit 67 to the infrared communication unit 64 by infrared communication. Here, the infrared communication unit 64 receives the patient information of the subject transmitted by the infrared communication unit 65 and transmits the received patient information of the subject to the control unit 66. On the other hand, the infrared communication unit 64 transmits the erasure instruction information for which the transmission instruction is given by the control unit 66 to the infrared communication unit 65 by infrared communication. The infrared communication unit 65 receives the erasure instruction information transmitted by the infrared communication unit 64 and transmits the received erasure instruction information to the control unit 67.

The control unit 66 of the main receiving device 63a has the same function as the function of the control unit 28 of the main receiving device 23a according to the second embodiment, and controls driving of the infrared communication unit 64 in place of the communication unit 12. The connection detector 25 detects a connection state between the communication unit 24 and the communication unit 31 under the control of the control unit 66, and transmits the connection detection result to the control unit 66.

The control unit 67 of the external monitor 63b has the same function as the function of the control unit 38 of the external monitor 23b according to the second embodiment, and controls driving of the infrared communication unit 65 in place of the communication unit 32. The connection detector 34 detects a connection state between the communication unit 24 and the communication unit 31, and a connection state between the portable recording medium 6 and the communication unit 33 under the control of the control unit 67, and transmits the connection detection results to the control unit 67. The control unit 67 of the external monitor 63b, on receiving the connection detection result indicating that the portable recording medium 6 is connected to the communication unit 33 from the connection detector 34, displays the connection mark indicating that the portable recording medium 6 and the communication unit 33 are in a connected state on the display unit 37, and displays the option 102 of the initialization mode on the display unit 37.

As described above, the fifth embodiment of the invention has the same function as that of the second embodiment, and is configured so as to transmit/receive the patient information of the subject or the erasure instruction information between the main receiving device and the external monitor by infrared communication instead of the cable communication employing the cable. Therefore, in addition to the enjoyment of the same effects and advantages of the second embodiment, the number of connectors arranged to detachably connect the cable can be reduced, and drip-proofness of the main receiving device and the external monitor can be easily guaranteed.

A sixth embodiment of the invention will be described. In the sixth embodiment, a receiving apparatus having the same function as that of the receiving apparatus 23 according to the second embodiment and an additional printing function for outputting a printed material to notify the subject of desirable information is provided.

FIG. 19 is a schematic diagram of one exemplary structure of an in-vivo information acquiring system according to the sixth embodiment of the invention. As shown in FIG. 19, the in-vivo information acquiring system according to the sixth embodiment includes a receiving apparatus 73 in place of the receiving apparatus 23 of the in-vivo information acquiring system according to the second embodiment. In other respects, the structure of the sixth embodiment is the same as the structure of the second embodiment, and the same elements are denoted by the same reference characters.

The receiving apparatus 73 includes the main receiving device 23a to which the receiving antennas 4a to 4h are connected, and an external monitor 73b which is detachably connected to the main receiving device 23a. The external monitor 73b, similarly to the external monitor 23b of the receiving apparatus 23 according to the second embodiment, is detachably connected to the main receiving device 23a via the cables 23c and 23d. Further, the external monitor 73b has the same function as that of the external monitor 23b of the receiving apparatus 23 according to the second embodiment, and additionally has a printing function to output a printed material to notify the subject of desirable information.

A structure of the receiving apparatus 73 according to the sixth embodiment of the invention will be described. FIG. 20 is a schematic block diagram of an exemplary structure of the receiving apparatus 73 according to the sixth embodiment. As shown in FIG. 20, the receiving apparatus 73 includes a control unit 78 in place of the control unit 38 of the external monitor 23b of the receiving apparatus 23 according to the second embodiment, and further includes a printer 74. In other respects, the structure of the sixth embodiment is the same as the structure of the second embodiment, and the same elements are denoted by the same reference characters.

The printer 74 outputs a printed material to notify the subject to whom the receiving apparatus 73 is attached of desirable information. Specifically, the printer 74 prints information, for which an output instruction is given by the control unit 78, on a medium such as a sheet of paper, and outputs a printed material such as a printed paper on which the information is printed. The information shown on the printed material includes, for example, precaution for the subject, prohibited matters, and a time to return the receiving apparatus 73 (in other words, a time the examination finishes).

The control unit 78 has the same function as the function of the control unit 38 of the external monitor 23b of the second embodiment. Further, the control unit 78 controls driving of the printer 74 based on the instruction information supplied from the input unit 36. Specifically, the control unit 78 controls the printer 74 to output a printed material on which desirable information is printed when the desirable information to notify the subject of is previously set and the instruction information giving the output instruction of the printed material is supplied from the input unit 36. Thus, the control unit 78 makes the printer 74 output the printed material on which the precaution for the subject, the prohibited matter, the time to return the receiving apparatus 73 (time of examination completion), or the like is printed. When the control unit 78 makes the printer 74 output the printed material on which the time to return the receiving apparatus 73 and the like are printed, the control unit 78 calculates a time (time of examination completion) the capsule endoscope 2 is discharged outside the subject based on a current time and makes the printer 74 print the time of examination completion as the time to return the receiving apparatus 73 on the printed material.

The printer 74 which is controlled as described above by the control unit 78 can output a printed paper 130 indicating, for example, the patient information A of the subject 1, the prohibited matter for the subject 1, and the time to return the receiving apparatus 73 as shown in FIG. 21. The printed paper 130 is delivered to the subject 1 to whom the receiving apparatus 73 is attached to notify the subject 1 of the information. Thus, the printer 74 can output the printed material which can notify the subject of desirable information.

In the sixth embodiment of the invention, the printer is arranged in the external monitor, though the invention is not limited thereto; and the printer may be arranged in the main receiving device. Then, the control unit of the main receiving device may be provided with a function of controlling the driving of the printer.

As described above, the sixth embodiment of the invention has the same function as that of the second embodiment, and further, is configured to output the printed material on which the desirable information is printed to notify the subject thereof. Therefore, in addition to the enjoyment of the same effects and advantages of the second embodiment, the desirable information such as the precaution for the subject, the prohibited matter, and the time to return the receiving apparatus can be easily notified to the subject.

In the first, the second, and the fourth to the sixth embodiments, the patient information of the subject is supplied to the receiving apparatus via the portable recording medium 6 such as a USB memory which has a predetermined connector as a media, however, the patient information of the subject may be supplied to the receiving apparatus with the use of a portable recording medium such as a CompactFlash® and an SD memory card which is detachably connected to a predetermined card slot as a media. The card slot for the connection of such a recording medium may be arranged in either of the main receiving device and the external monitor.

As can be seen from the foregoing, the receiving apparatus and the in-vivo information acquiring system employing the same according to the invention are useful for the acquisition of the images of an interior of the organs as acquired through image capturing by the capsule endoscope introduced inside the subject, and more particularly, suitable as a receiving apparatus which can prevent mismatching between the subject carrying the receiving apparatus and the image of the interior of the organ received by the receiving apparatus (i.e., mix-up of the test bodies), and the in-vivo information acquiring system employing the above receiving apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A receiving apparatus comprising:
   a receiving unit which receives image data acquired through image capturing by a capsule endoscope introduced inside a subject;
   a reader to which a portable recording medium on which identification information identifying the subject is recorded in an erasable manner is detachably connected, the reader being configured to read out the identification information of the subject in the recording medium after the receiving apparatus is attached to the subject and to associate the received image data with the identification information;
   a display unit which displays the identification information of the subject read out by the reader; and
   a control unit which controls registration of the identification information of the subject displayed by the display unit and which is configured to erase the registered identification information of the subject remaining in the recording medium under control of the receiving apparatus, after the identification information is registered in the receiving apparatus.

2. The receiving apparatus according to claim 1, wherein the portable recording medium is connected to the receiving apparatus after the receiving apparatus is attached to the subject, and
   while the portable recording medium being connected to the receiving apparatus, the identification information of the subject is displayed in the display unit and the registered identification information of the subject remaining in the portable recording medium is erased after the identification information is registered in the receiving apparatus.

3. The receiving apparatus according to claim 1, further comprising:
   a connection detector that detects a connection of the portable recording medium; wherein
   identification information of the subject in the portable recording medium is read out if the connection of the portable recording medium is detected.

4. The receiving apparatus according to claim 1, further comprising
   a printer which outputs a printed material on which desirable information to be notified to the subject is printed.

5. The receiving apparatus according to claim 1, wherein the control unit initializes the receiving apparatus based on the registered identification information of the subject which is an examination target of the receiving apparatus, and sequentially accumulates the image data acquired through the image capturing by the capsule endoscope as image data of the subject identified by the identification information.

6. The receiving apparatus according to claim 1, wherein the receiving unit and the control unit are arranged in a main receiving device, and
   the reader and the display unit are arranged in an external display unit which is detachably connected to the main receiving device.

7. The receiving apparatus according to claim 1, wherein plural pieces of identification information of plural test bodies including at least the identification information of the subject are recorded on the recording medium, and
   the receiving apparatus further comprises a selection instructing unit which gives a selection instruction of the identification information of the subject from the plural pieces of identification information of the plural test bodies,
   the display unit displays a list of the plural pieces of identification information of the plural test bodies, and
   the control unit registers the identification information of the subject selected by the selection instructing unit from the plural pieces of identification information of the plural test bodies.

8. The receiving apparatus according to claim 7, wherein the selection instructing unit is an input unit which inputs selection instruction information to give the selection instruction of the identification information of the subject from the plural pieces of identification information of the plural test bodies displayed as the list by the display unit.

9. The receiving apparatus according to claim 7, wherein the selection instructing unit is an ID reader which reads out the identification information recorded in an ID tag carried by the subject, and
the control unit registers the identification information of the subject which matches with the identification information read out by the RFID reader from plural pieces of identification information of the plural test bodies.

10. The receiving apparatus according to claim 9, wherein the ID reader is an RF-ID reader, and the ID tag is an RF-ID tag.

11. A receiving apparatus comprising:
an external display unit which includes a recording medium on which identification information identifying a subject is recorded in an erasable manner and a display unit which is configured to display the identification information of the subject in the recording medium after the receiving apparatus is attached to the subject; and
a main receiving device which includes a receiving unit which is detachably connected to the external display unit and receives image data acquired through image capturing by a capsule endoscope introduced inside the subject, and a control unit which controls registration of the identification information of the subject displayed by the display unit and which is configured to erase the registered identification information of the subject remaining in the recording medium under control of the main receiving device, after the identification information is registered in the receiving apparatus.

12. The receiving apparatus according to claim 11, wherein the main receiving device includes an infrared communication unit which performs infrared communication with the external display unit, and
the identification information of the subject is transmitted to the main receiving device from the external display unit by the infrared communication.

13. The receiving apparatus according to claim 11, wherein the control unit initializes the receiving apparatus based on the registered identification information of the subject which is an examination target of the receiving apparatus, and sequentially accumulates image data acquired through the image capturing by the capsule endoscope as image data of the subject identified by the identification information.

14. The receiving apparatus according to claim 11, wherein the control unit sends erasure instruction information to instruct erasure of the registered identification information of the subject to the external display unit, and
the external display unit performs processing to erase the identification information of the subject designated in the erasure instruction information, the identification information being recorded on the recording medium, on receiving the erasure instruction information.

15. The receiving apparatus according to claim 11, wherein plural pieces of identification information of plural test bodies including at least the identification information of the subject are recorded on the recording medium,
the receiving apparatus further comprises a selection instructing unit which gives a selection instruction of the identification information of the subject from the plural pieces of identification information of the plural test bodies,
the display unit displays a list of the plural pieces of identification information of the plural test bodies, and
the control unit registers the identification information of the subject selected by the selection instructing unit from the plural pieces of identification information of the plural test bodies.

16. The receiving apparatus according to claim 15, wherein the selection instructing unit is an input unit which inputs selection instruction information to give the selection instruction of the identification information of the subject from the plural pieces of identification information of the plural test bodies displayed as the list by the display unit.

17. The receiving apparatus according to claim 15, wherein the selection instructing unit is an ID reader which reads out the identification information recorded in an ID tag carried by the subject, and
the control unit registers the identification information of the subject which matches with the identification information read out by the RFID reader from the plural pieces of identification information of the plural test bodies.

18. The receiving apparatus according to claim 17, wherein the ID reader is an RF-ID reader, and the ID tag is an RF-ID tag.

19. An in-vivo information acquiring system, comprising:
a portable recording medium on which identification information identifying a subject is recorded in an erasable manner; and
a receiving apparatus which is detachably connected to the recording medium, after the receiving apparatus is attached to the subject, and is configured to display the identification information of the subject read out from the recording medium, to register the identification information of the subject displayed, and to erase the registered identification information of the subject remaining in the recording medium under control of the receiving apparatus, and to receive image data acquired through image capturing by a capsule endoscope inside the subject after the identification information is registered in the receiving apparatus.

20. The in-vivo information acquiring system according to claim 19, further comprising a device that manages identification information of a plurality of subjects, the identification information including a first identification of a first subject; wherein
when the first identification information is written into the portable recording medium from the device, the device affixes an information indicating that the first identification information is taken out, to the original first identification information in the device, and
when the first identification information is returned to the device, together with the image data, the device deletes the information affixed to the original first identification information.

21. The in-vivo information acquiring system according to claim 19, wherein
the receiving apparatus initializes the receiving apparatus based on the registered identification information of the subject which is an examination target of the receiving apparatus, and sequentially accumulates image data acquired through the image capturing by the capsule endoscope as image data of the subject identified by the identification information.

22. The in-vivo information acquiring system according to claim 19, wherein
the receiving apparatus includes
an external display unit which includes a reader that is detachably connected to the recording medium, reads out the identification information of the subject in the recording medium, and a display unit that displays the identification information of the subject read out by the reader, and a main receiving device which includes a receiving unit that is detachably connected to the external display unit, and receives the image data acquired through the image capturing by the capsule endoscope in the subject, and a control unit that controls registration of the identification information of the subject displayed by the display unit, and erasure of the registered identification information of the subject remaining in the recording medium.

23. The in-vivo information acquiring system according to claim 19, wherein the control unit sends erasure instruction information to instruct erasure of the registered identification information of the subject to the external display unit, and the external display unit performs processing to erase the identification information of the subject designated in the erasure instruction information, the identification information being recorded on the recording medium, on receiving the erasure instruction information.

24. The in-vivo information acquiring system according to claim 19, further comprising a management unit which manages plural pieces of identification information of plural test bodies including the identification information of the subject in an integrated manner, wherein the plural pieces of identification information of plural test bodies managed by the management unit in an integrated manner are recorded on the recording medium.

25. An in-vivo information acquiring system, comprising:

an external display unit which includes a recording medium on which identification information identifying a subject is recorded in an erasable manner and a display unit that is configured to display the identification information of the subject in the recording medium after the receiving apparatus is attached to the subject, and a main receiving device which includes a receiving unit that is detachably connected to the external display unit and receives the image data acquired through image capturing by a capsule endoscope inside the subject, and a control unit which controls registration of the identification information of the subject displayed by the display unit and which is configured to erase the registered identification information of the subject remaining in the recording medium under control of the main receiving device, after the identification information is registered.

26. The in-vivo information acquiring system according to claim 25, wherein the control unit initializes the receiving apparatus based on the registered identification information of the subject which is an examination target of the receiving apparatus, and sequentially accumulates image data acquired through the image capturing by the capsule endoscope as image data of the subject identified by the identification information.

27. The in-vivo information acquiring system according to claim 25, further comprising a management unit which manages plural pieces of identification information of plural test bodies including the identification information of the subject in an integrated manner, wherein the plural pieces of identification information of the test bodies managed by the management unit in an integrated manner are recorded on the recording medium.

28. An information registration method, comprising:

reading identification information of a subject from a recording medium which is portable and on which the identification information identifying the subject is recorded in an erasable manner after a receiving apparatus is attached to the subject;

displaying the identification information of the subject read out in the reading;

registering the identification information of the subject read out in the reading;

erasing the registered identification information of a subject remaining in a recording medium under control of the receiving apparatus, after registering the identification information on the receiving apparatus.

29. The information registration method according to claim 28, further comprising:

sequentially accumulating image data acquired through image capturing by a capsule endoscope introduced inside the subject as image data of the subject identified by the identification information.

30. The information registration method according to claim 28, further comprising instructing a selection of the identification information of the subject from plural pieces of identification information of plural test bodies, wherein the registering includes registering the identification information of the subject selected in the instructing.

31. The information registration method according to claim 28, further comprising:

sending erasure instruction information to instruct erasure of the registered identification information of the subject from a main receiving device side to an external display unit which is connected to the main receiving device and to which the recording medium is connected; and erasing the identification information of the subject designated in the erasure instruction information, the identification information being recorded on the recording medium, when the erasure instruction information is received by the external display unit.

* * * * *